(12) United States Patent
Connell et al.

(10) Patent No.: US 12,329,320 B2
(45) Date of Patent: Jun. 17, 2025

(54) MODULAR BLENDER WITH IMPROVED WATER HEATING AND LIGHT BEAM DETECTION

(71) Applicant: F'real! Foods, LLC, Emeryville, CA (US)

(72) Inventors: Steven T. Connell, Oakland, CA (US); John Diemer, Lafayette, CA (US); Kathleen A. Scheible, San Francisco, CA (US); Kurt J. Ahmann, San Francisco, CA (US); Patrick M. Goebel, San Francisco, CA (US); Shek Fai Lau, Foster City, CA (US); Curtis Tom, San Mateo, CA (US)

(73) Assignee: F'real! Foods, LLC, Emeryville, CA (US)

( * ) Notice: Subject to any disclaimer, the term of this patent is extended or adjusted under 35 U.S.C. 154(b) by 1023 days.

(21) Appl. No.: 17/156,952

(22) Filed: Jan. 25, 2021

(65) Prior Publication Data

US 2021/0212519 A1    Jul. 15, 2021

Related U.S. Application Data

(62) Division of application No. 15/353,656, filed on Nov. 16, 2016, now Pat. No. 10,898,031.

(51) Int. Cl.
*A47J 43/044* (2006.01)
*A47J 31/42* (2006.01)
(Continued)

(52) U.S. Cl.
CPC ............. *A47J 43/044* (2013.01); *A47J 31/42* (2013.01); *A47J 43/0755* (2013.01);
(Continued)

(58) Field of Classification Search
CPC ... B01F 35/602; B01F 35/605; B01F 35/6052
See application file for complete search history.

(56) References Cited

U.S. PATENT DOCUMENTS

| 4,702,611 A | 10/1987 | Crossley |
| 4,736,600 A | 4/1988 | Brown |
| (Continued) | | |

FOREIGN PATENT DOCUMENTS

| CN | 1642847 A | 7/2005 |
| CN | 102164843 A | 8/2011 |
| (Continued) | | |

OTHER PUBLICATIONS

Notice of Preliminary Rejection from Korean Patent Office for related Application No. 10-2019-7016815 dated Dec. 28, 2021 (7 Pages including English Translation).

(Continued)

*Primary Examiner* — Marc C Howell
(74) *Attorney, Agent, or Firm* — Michael Best & Friedrich LLP

(57) ABSTRACT

A method of operating a blender having a rotatable cutting blade in a food preparation chamber includes providing a sensing light assembly, generating at least one sensing light beam below the food preparation chamber, inserting a cup containing food to be blended into the food preparation chamber, generating an error signal if a foreign object crosses the sensing light beam, and preventing or stopping rotation of the cutting blade in response to the error signal.

21 Claims, 28 Drawing Sheets

(51) Int. Cl.
*A47J 43/07* (2006.01)
*B01F 27/805* (2022.01)
*B01F 27/806* (2022.01)
*B01F 33/83* (2022.01)
*B01F 35/10* (2022.01)
*B01F 35/11* (2022.01)
*B01F 35/60* (2022.01)
*A61L 2/07* (2006.01)
*B01F 33/80* (2022.01)
*B01F 101/13* (2022.01)

(52) U.S. Cl.
CPC .......... *B01F 27/805* (2022.01); *B01F 27/806* (2022.01); *B01F 33/83* (2022.01); *B01F 35/11* (2022.01); *B01F 35/1452* (2022.01); *B01F 35/6052* (2022.01); *A47J 2043/04454* (2013.01); *A61L 2/07* (2013.01); *A61L 2202/11* (2013.01); *B01F 33/83611* (2022.01); *B01F 2101/13* (2022.01)

(56) References Cited

U.S. PATENT DOCUMENTS

| | | | |
|---|---|---|---|
| 5,640,783 A | 6/1997 | Schumaier | |
| 5,803,377 A | 9/1998 | Farrell | |
| 5,962,060 A | 10/1999 | Farrell | |
| 6,041,961 A | 3/2000 | Farrell | |
| 6,318,889 B1 | 11/2001 | Hansen, Sr. | |
| 6,326,047 B1 | 12/2001 | Farrell | |
| 6,465,034 B2 | 10/2002 | Farrell | |
| 6,474,862 B2 | 11/2002 | Farrell | |
| 6,527,207 B1 | 3/2003 | Farrell et al. | |
| 6,848,356 B1 | 2/2005 | Mueller | |
| 7,144,150 B2 | 12/2006 | Farrell | |
| 7,520,658 B2 | 4/2009 | Farrell | |
| 7,520,662 B2 | 4/2009 | Farrell | |
| 8,336,731 B2 | 12/2012 | Farrell et al. | |
| 8,763,515 B2 | 7/2014 | Farrell et al. | |
| 8,905,626 B2 | 12/2014 | Farrell et al. | |
| 9,370,279 B2* | 6/2016 | Pineda ................. | A47J 43/0716 |
| 9,386,882 B2 | 7/2016 | Farrell et al. | |
| 9,420,917 B2 | 8/2016 | Farrell et al. | |
| 9,629,503 B2* | 4/2017 | Vu ....................... | A47J 43/0716 |
| 10,898,031 B2 | 1/2021 | Connell et al. | |
| 2010/0203209 A1 | 8/2010 | Fishbein et al. | |
| 2011/0088568 A1 | 4/2011 | Farrell et al. | |
| 2011/0090756 A1* | 4/2011 | Farrell .................... | B08B 9/00 366/138 |
| 2012/0121780 A1 | 5/2012 | Lai et al. | |
| 2013/0344220 A1 | 12/2013 | Farrell et al. | |
| 2013/0344221 A1 | 12/2013 | Farrell et al. | |
| 2015/0190014 A1 | 7/2015 | Farrell et al. | |
| 2015/0265983 A1* | 9/2015 | Fleming .............. | B01F 35/2131 366/206 |
| 2016/0220069 A1 | 4/2016 | Gardner et al. | |
| 2016/0270598 A1 | 9/2016 | Vu et al. | |
| 2018/0020875 A1* | 1/2018 | Kolar .................. | A47J 43/0777 366/279 |

FOREIGN PATENT DOCUMENTS

| | | |
|---|---|---|
| CN | 102802477 A | 11/2012 |
| CN | 103298383 A | 9/2013 |
| CN | 103391735 A | 11/2013 |
| CN | 103402403 A | 11/2013 |
| CN | 204182340 U | 3/2015 |
| CN | 105916418 A | 8/2016 |
| GB | 191011245 B | 5/1911 |
| WO | WO2014009904 A2 | 1/2014 |
| WO | 2015038360 A1 | 3/2015 |

OTHER PUBLICATIONS

Office Action issued from The Brazilian Patent Office for related Application No. BR112019009609-4 (6 Pages including English Translation).
Australian Patent Office Action for Related Application No. 2017361264 dated Nov. 17, 2022 (4 pages).
International search Report with Written Opinion for related Application No. PCT/US17/61883 dated Mar. 26, 2018 (11 Pages).
Notice of Deficiencies for related Application No. 266508 issued from the Israel Patent Office dated May 4, 2022 (5 Pages).
Chinese Patent Office Action for Application No. 2022101160290, dated Mar. 22, 2024 (12 pages with machine translation).
Canadian Patent Office. Office Action for Application No. 3,042,053, dated Jan. 12, 2024 (4 pages).
Korean Patent Office Action for Application No. 10-2022-7042155, dated Feb. 28, 2024 (8 pages with translation).
Chinese Patent Office Action for Application No. 202210116029.0 dated Mar. 22, 2024 (14 pages with English machine translation).
Israeli Patent Office Action for Application No. 308287 dated Mar. 27, 2024 (4 pages).
New Zealand Patent Office Action for Application No. 780286 dated May 31, 2024 (4 pages).
New Zealand Patent Office Action for Application No. 794516 dated Jun. 14, 2024 (4 pages).
New Zealand Patent Office Action for Application No. 794518 dated Jun. 19, 2024 (3 pages).
Chinese Patent Office Action for Application No. 202210116029.0 dated Jun. 24, 2024 (8 pages with English machine translation).

* cited by examiner

MODULAR BLENDER WITH IMPROVED WATER HEATING AND LIGHT BEAM DETECTION

FIELD OF THE INVENTION

The present invention relates to food preparation machines, particularly electrical blenders for preparing smoothies, milkshakes, protein shakes and other blended beverages.

BACKGROUND OF THE INVENTION

Blended fruit smoothies, milkshakes and protein shakes are popular among health conscious people. In these blended drinks, dairy, fresh fruits and/or vegetables can be mixed together with, if desired, vitamins and protein supplements to provide fresh nutritious foods in a convenient, portable form.

While it is advantageous to blend carefully selected ingredients at the peak of their freshness, it is often not practical to do so. To have fresh fruits and vegetables available every day, for example, one may need to frequently go shopping for such fruits/vegetables, give the fruits/vegetables time to ripen and then make sure that the fruits/vegetables do not over ripen. Moreover, working with fresh fruits and vegetables usually generates organic wastes, is often messy and inevitably requires clean up. This means a lot of time and attention.

In a fast moving society, there is a demand for a fresh, nutritious blended drink that can be selected and prepared quickly. Better yet, such a fresh, blended drink should be available at a place that can be easily accessed, such as a convenience store, restaurant or one's home.

f'real Foods, LLC, a subsidiary of Rich Products Corporation, has made a business of making fresh, nutritious smoothies and milkshakes available at easily accessible locations, such as convenience stores. f'real Foods starts with fresh ingredients, such as fresh fruits and milk, which it pre-blends into smoothies and milkshakes. The pre-blended smoothies and milkshakes are then hard frozen in sealed cups before they are shipped to convenience stores at many different locations. The frozen pre-blended smoothies and milkshakes are then stored in a freezer at the convenience store next to a commercial size blending machine. When the convenience store consumer wants a fresh smoothie or milkshake, the consumer simply selects the desired frozen, pre-blended smoothie or milkshake from the convenience store freezer, tears the seal off the top of the smoothie/milkshake cup and then places the smoothie/milkshake cup in a cupholder built into the blending machine. The consumer can then start the blending machine to blend the frozen smoothie/milkshake to a desired consistency.

f'real Foods, LLC has numerous U.S. patents and U.S. published patent applications covering its blending machines and processes for preparing smoothies/milkshakes, including U.S. Pat. Nos. 5,803,377; 5,962,060; 6,041,961; 6,326,047; 6,474,862; 6,465,034; 6,527,207; 7,144,150; 7,520,658; 7,520,662; 8,336,731; 8,763,515; 8,902,626; 9,386,882 and 9,420,917 as well as U.S. Published Patent Application Nos. 2011/0088568; 2013/0344220; 2013/0344221 and 2015/0190014, the disclosures of which are all hereby incorporated by reference.

For its convenience store market, f'real has supplied heavy duty, stainless steel commercial size blenders that can withstand rugged use by convenience store consumers. These heavy duty blenders are typically attached to a municipal water supply so that they have a generous supply of water for blending, and autonomous self-cleaning and sanitizing. After a milkshake or smoothie is blended and removed by the consumer, the food preparation chamber in the f'real heavy-duty blender is automatically sprayed with water, preferably heated water, to wash away any food residue. To have a supply of heated cleaning water readily available, the water within f'real's heavy duty blender is heated in a water heater and stored in an accumulator having a flexible diaphragm. For added cleanliness, many of f'real's heavy duty blenders are equipped with a steamer to periodically kill any bacteria that might be present in the food preparation chamber.

While f'real's heavy duty, commercial size blenders have worked well in the convenience store setting, there has been a strong demand from convenience store owners to obtain blenders with the same (or better) heavy duty qualities but with improved design for assembly and service. Such an improved blender would lower the cost to convenience store owners by reducing even further the small amount of effort and expense they devote to maintenance and repair. Finally, as always, it is important to continue improving the safety and ease of use for f'real's blenders.

BRIEF SUMMARY OF THE INVENTION

The present invention is directed to an economical food or beverage blender that is especially suited for blending frozen milkshakes and smoothies. This blender is preferably built with an internal frame and modules to allow its quick, easy and cost-effective manufacture. In the preferred embodiment, a single piece internal frame is used. This internal frame is preferably injection molded from a hard, durable plastic. On its front side, this internal frame is designed to precisely accommodate and align a belt-driven cupholder elevator assembly. On its rear side, the internal frame preferably accommodates slide-in water heater and steamer assembly trays. Preferably, the internal frame further supports a mix motor assembly, a food preparation chamber, an optional video screen, a control panel, microprocessor controlled electrical components and the blender's external housing.

To reduce plumbing connections and costs, the water heater preferably both stores a sizable volume of water and contains coils for heating that water. Because water will be drained quickly from the water heater during a cleaning cycle, the heating coils are preferably placed toward the bottom of the water heater so that the heating coils will always be immersed in water and, thereby, avoid overheating. Similarly, the steamer heating coils are preferably placed toward the bottom of the steamer. The steamer preferably has two roles, providing a shot of hot water into the cup to aid the blending process and periodically steam sanitizing the food preparation chamber after blending. Because the steamer uses different amounts of water for each of these roles, a valve and flowmeter are used to carefully control how much water enters the steamer. At its input, the steamer preferably uses an input down tube to insert water where it will not quench the boiling of water. At its output, seamless polytetrafluoroethylene (PTFE) tubing is preferably used to transport hot water and steam from the steamer to the food preparation chamber. This PTFE tubing resists scale deposits to reduce the need for maintenance.

To expedite manufacture and assure alignment, the drive belt portion of the cupholder elevator assembly is preferably configured to snap into a lower receiving port on the internal frame. To allow this snap-in manufacture, the toe of an idler assembly for the drive belt is inserted into the receiving port and then the heel of the idler assembly is bolted onto the internal frame. A spring in the idler assembly automatically sets the drive belt to the correct tension.

To promote safety, crisscrossing infrared light beams are preferably placed at the entrance of the food preparation chamber. One set of light beams is used to detect whether the cup entering the food preparation chamber is the correct size. A second set of light beams is used to detect whether any foreign object, such as a customer's hand, is below the food preparation chamber. If the light beam(s) detect an object entering the food preparation chamber that is inconsistent with the safe operation of the blender, blending processes will be immediately blocked or discontinued.

DETAILED DESCRIPTION OF THE INVENTION

Figure 1:
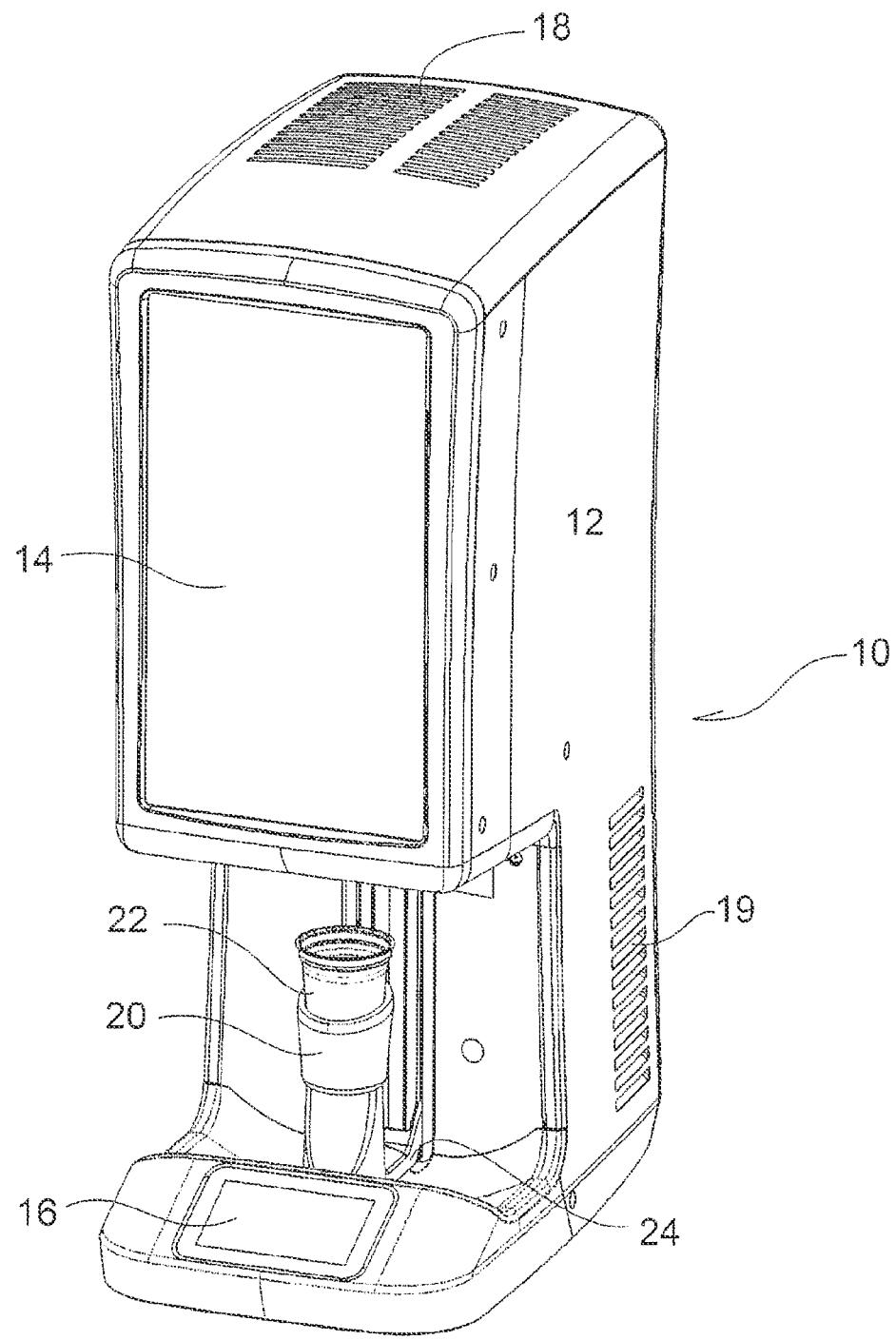
FIG. 1 illustrates a front perspective view of a preferred blender of the present invention.
Figure 2:
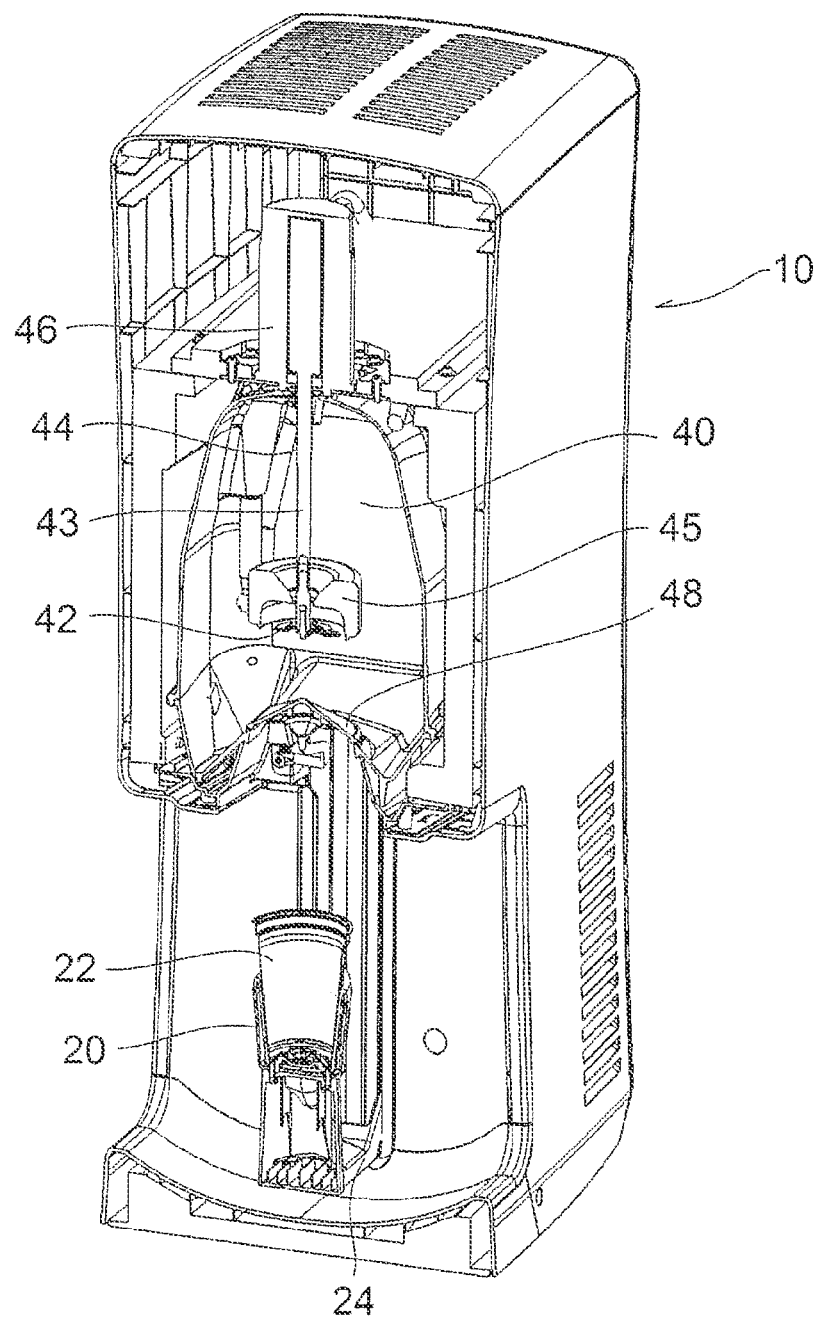
FIG. 2 illustrates a cut-away front perspective view of the FIG. 1 blender.
Figure 3:
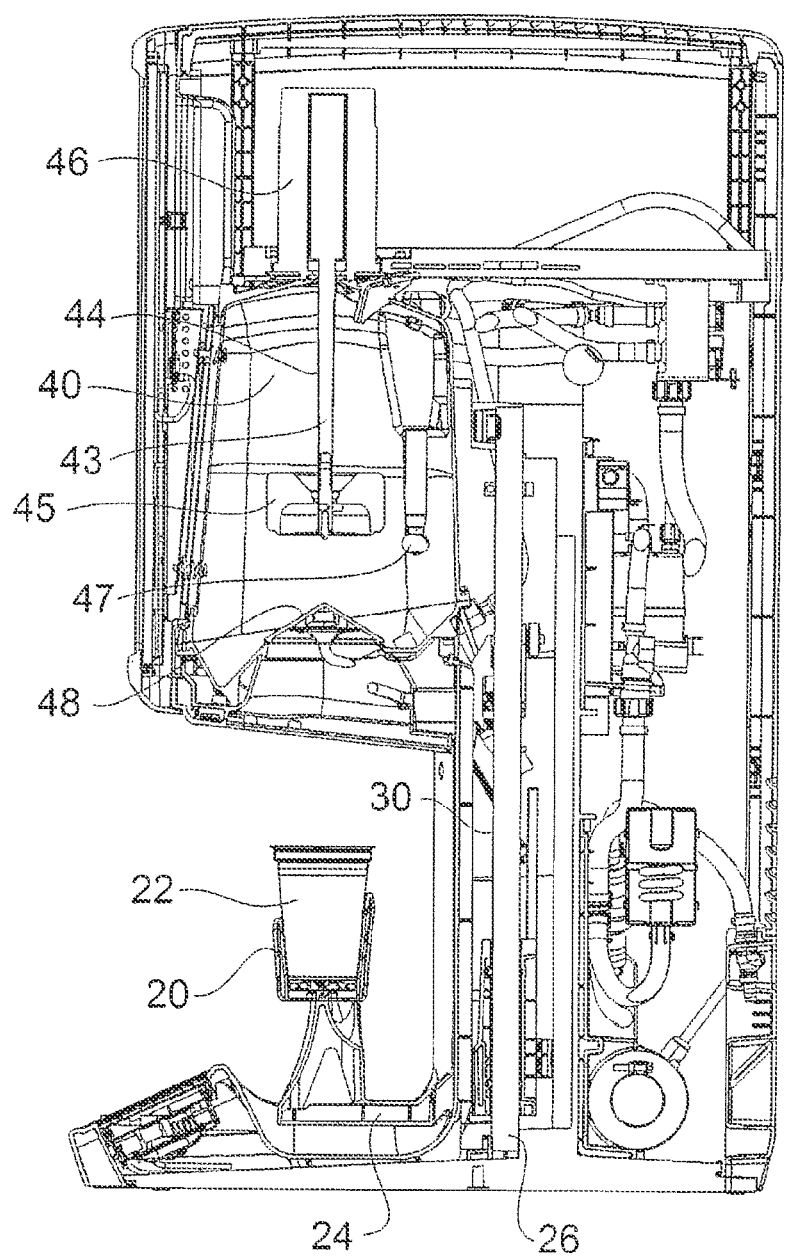
FIG. 3 illustrates a cut away right side view of the FIG. 1 blender.

FIG. 1 illustrates a preferred blender 10 of the present invention as it would be viewed from the outside. This blender 10 preferably has an external housing 12 (to protect the blender's internal working components) with heat dissipating vents 18, 19, an optional video screen 14, a control panel 16, a cupholder 20, a cantilevered cupholder connector 24 and a cup 22 nested inside the cupholder 20. The cup 22 holds the food or beverage to be blended. The blender 10 of the present invention is particularly useful for blending frozen milkshakes and smoothies. Nonetheless, those of skill in the art will ready recognize that other types of food products, beverages or materials can also be blended using the blender 10 of the present invention. The optional video screen 14 is preferably at eye level for the user and is useful to provide instructions on how to use the blender 10, advertisements and/or visual entertainment. The optional video screen 14 can also tell the user if the blender 10 is being improperly operated and needs to be reset. The control panel 16 allows the user to initiate the blending process. The control panel 16 may also be used to provide instructions on how to use the blender 10, advertisements and/or visual entertainment. The user first places a cup 22 filled with food, beverage or other material in the cupholder 20. The user then presses one or more buttons on the control panel 16 to start the blender 10. In the preferred embodiment, the control panel 16 is a touchscreen which may provide the user with one or more choices, such as a thick, medium or thin milkshake or smoothie consistency. Alternatively, the control panel 16 could provide the user with a simple "start" button, FIGS. 2 and 3 provide cut-away front and side views of the preferred blender 10 of the present invention. Through a cantilevered cupholder connector 24, the cupholder 20 is connected to a cupholder elevator assembly 30 (which is better seen in FIG. 16). To begin the blending process, the cupholder elevator assembly 30 lifts the cup 22 and cupholder 20 from the FIG. 1 starting position into the food preparation chamber 40 through the flip-up food preparation chamber door 48 so that the food, beverage or other material in the cup 22 can be placed into contact with the sharp rotatable cutting blade 42 of the mix motor assembly 44. The mix motor assembly 44 has a spindle 43 which connects the sharp rotatable blade 42 to mix motor 46. To minimize spills during the blending process, a weighted splash shield 45 is preferably placed concentrically on the spindle 43 shaft. As the cup 22 is raised by the cupholder elevator assembly 30 prior to blending, the splash shield 45 automatically covers the top opening of the cup 22. Preferred forms of weighted splash shield 45 are more fully described in f'real's U.S. Pat. Nos. 7,520,658 and 8,763,515. A preferred form of sharp rotatable cutting blade 42 for the mix motor assembly is described in f'real's U.S. Pat. No. 6,527,207. During the blending process, the mix motor 46 spins the sharp rotatable cutting blade 42 in the cup 22 as the cup 22 is moved up and down by cupholder elevator assembly 30. The weighted splash shield 45 is preferably free floating during the blending process so that it can easily move up and down with the cup 22. After the blending process is completed, the cupholder elevator assembly 30 lowers the cup 22 back through the flip-up food preparation chamber door 48 until the cup 22 and cupholder 20 reach their original starting position as shown in FIG. 1. As the cup 22 is being lowered, the weighted splash shield 45 automatically disconnects from the cup 22 when it is blocked from further downward movement by a stop bar (not shown) placed on the spindle 43 above the sharp rotatable cutting blade 42.

The cup 22 and cupholder 20 preferably have mating anti-rotational surfaces (not shown) to prevent the cup 22 and cupholder 20 from rotating with respect to one another during the blending process. Preferred anti-rotational surfaces are described in f'real's U.S. Pat. Nos. 8,336,731 and 6,041,961.

Figure 4:
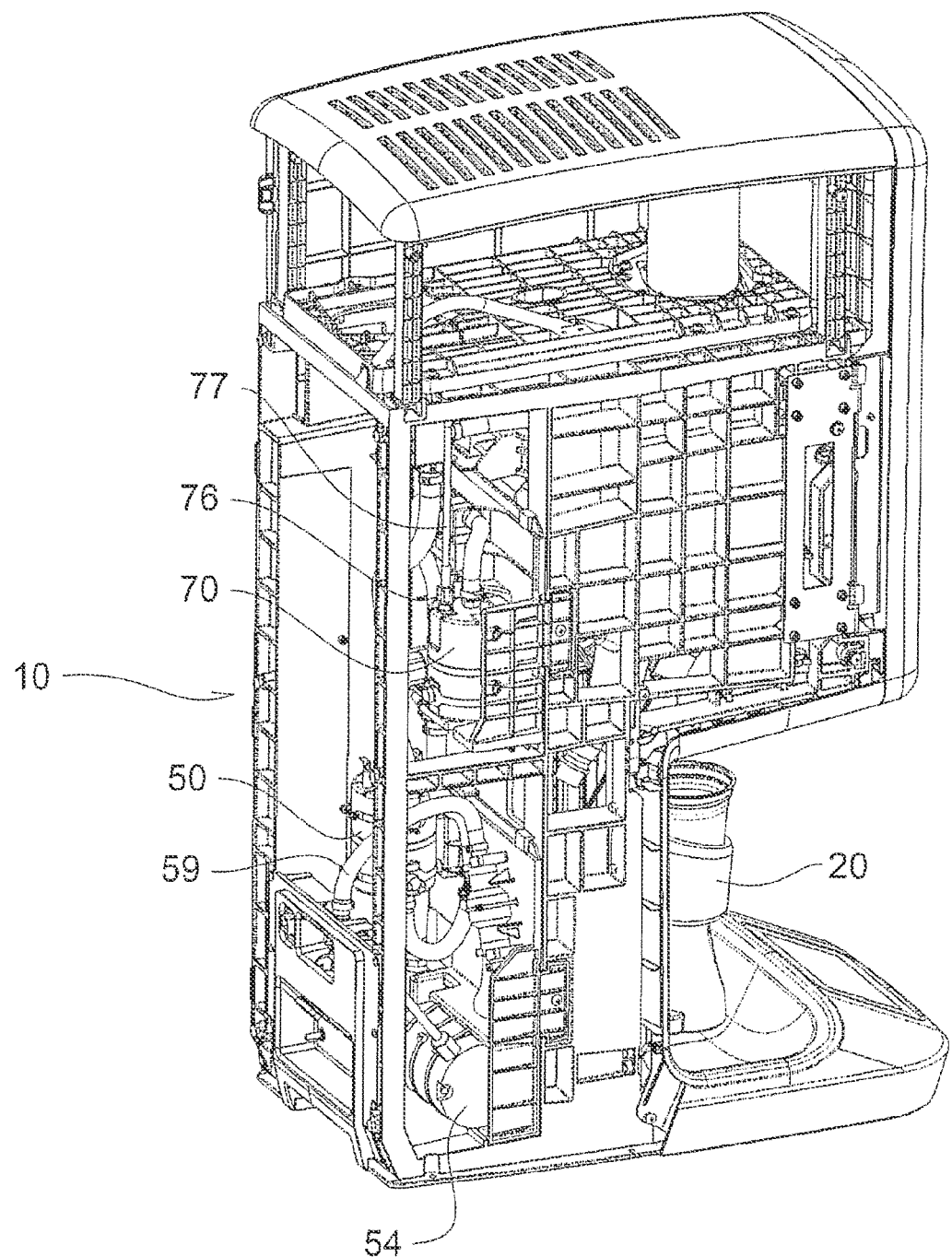
FIG. 4 illustrates a cut-away rear perspective view of FIG. 1 blender.

FIG. 4 provides a cut-away rear view of the preferred blender 10 of the present invention illustrating important sanitation components for the blender 10. To keep the food preparation chamber 40 and its moving parts clean between blending processes, hot water is preferably sprayed around the blending chamber through multiple nozzles, including nozzle 47 (FIG. 3). In the preferred embodiment, the hot water comes from water heater 50. This hot water cleans the walls of the food preparation chamber 40, the weighted splash shield 45, the spindle 43 and the sharp rotatable cutting blade 42. A drain (not shown) is placed at the bottom of the food preparation chamber 40 to remove dirty cleaning water. A preferred arrangement of rinse cleaning components is described in f'real's U.S. Pat. No. 7,520,662. Hot rinse cleaning is preferably done after every blending process. To kill bacteria and disinfect, hot steam is preferably routed into the food preparation chamber at appropriate intervals. The hot steam comes from steamer 70. While it is usually not necessary to steam clean the food preparation chamber after every blending process, steam cleaning should be done at least once a day and can be done more frequently, if needed.

As shown in FIGS. 5-8, the water heater 50 and associated components form water heater assembly 60 and are preferably contained on water heater tray 58. Similarly, the steamer 70 and related components form steamer assembly 68 and are preferably contained on steamer tray 72. These modular assemblies 60, 68 allow the blender 10 of the present invention to be more easily assembled. They also allow the blender 10 to be more easily maintained. For example, if a problem develops at a convenience store with a water heater 50, the convenience store owner can simply disconnect the hoses 51, 53, 59 (see, FIG. 4 and FIG. 9) and electrical wiring (not shown) which connect the water heater assembly 60 to the rest of the blender 10 and then remove the water heater assembly 60. The convenience store owner can then be shipped a new water heater assembly 60 by the blender manufacturer to use in repairing the blender 10 by connecting the new water heater assembly hoses 51, 53, 59 and electrical wiring. In this manner, the convenience store owner does not need to individually take apart and try to fix any of the components of the water heater assembly 60. Likewise, the convenience store owner does not need to try to troubleshoot the problem with the water heater assembly. So long as the convenience store owner can identify that there is a problem associated with the water heater components, the blender 10 can be fixed by simply substituting a new water heater assembly 60. The broken water heater assembly 60 can then be shipped back to the blender manufacturer for a more detailed assessment of the water heater problem.

Figure 5:
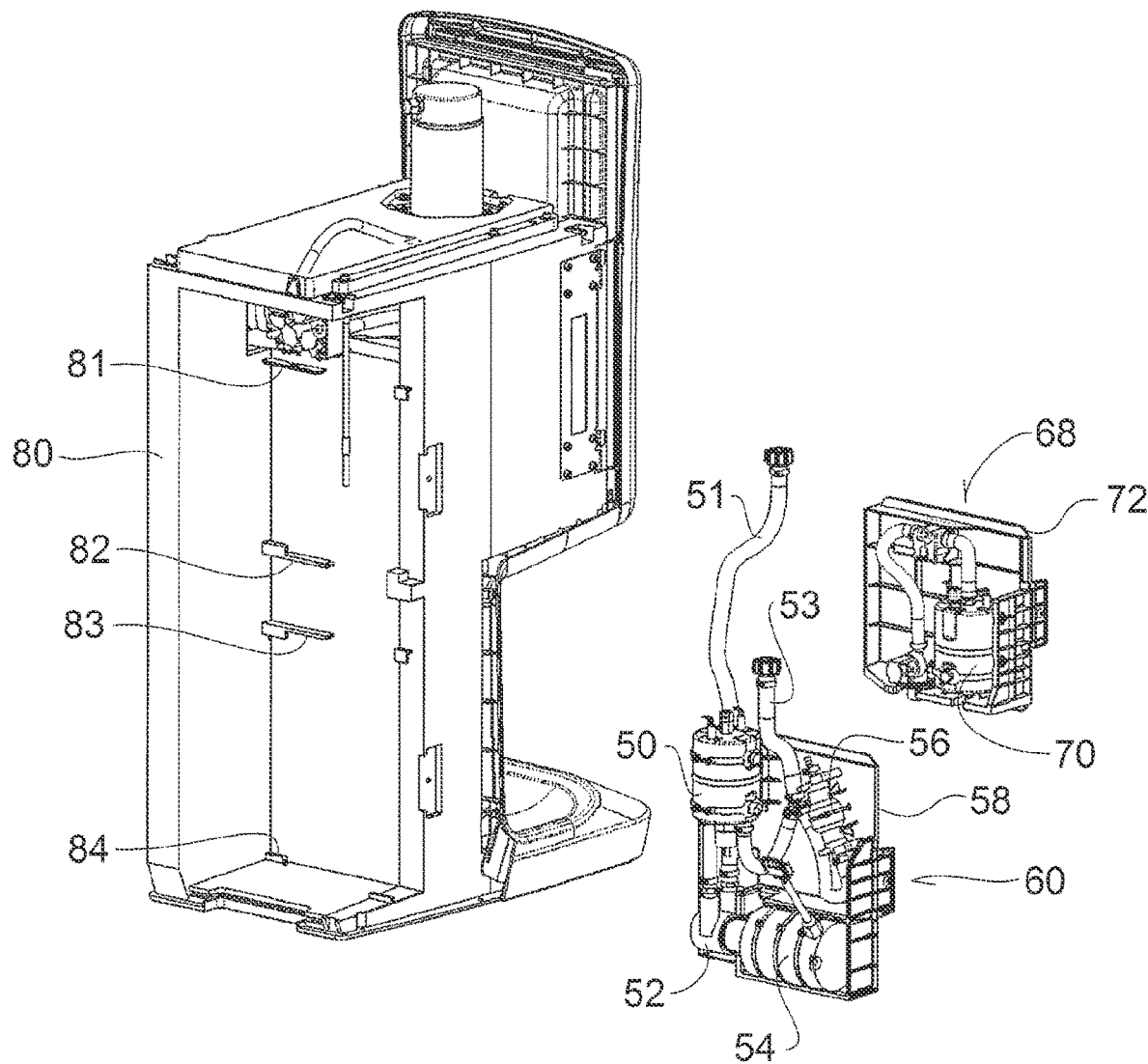
FIG. 5 illustrates a cut-away rear view of the FIG. 1 blender with the water heater assembly and steamer assembly trays removed.
Figure 6:
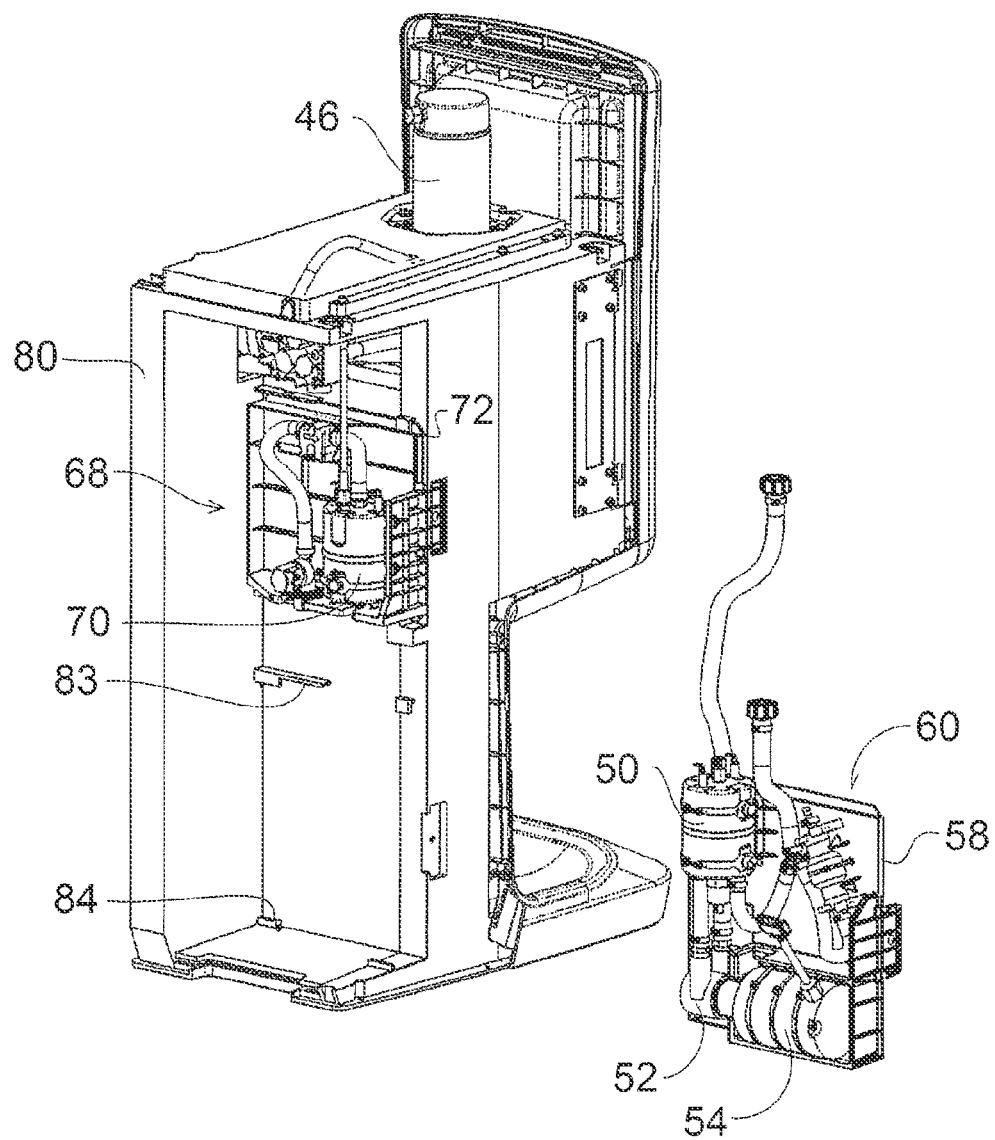
FIG. 6 illustrates the cut-away rear view of the FIG. 5 blender with the steamer assembly tray reinserted.
Figure 7:
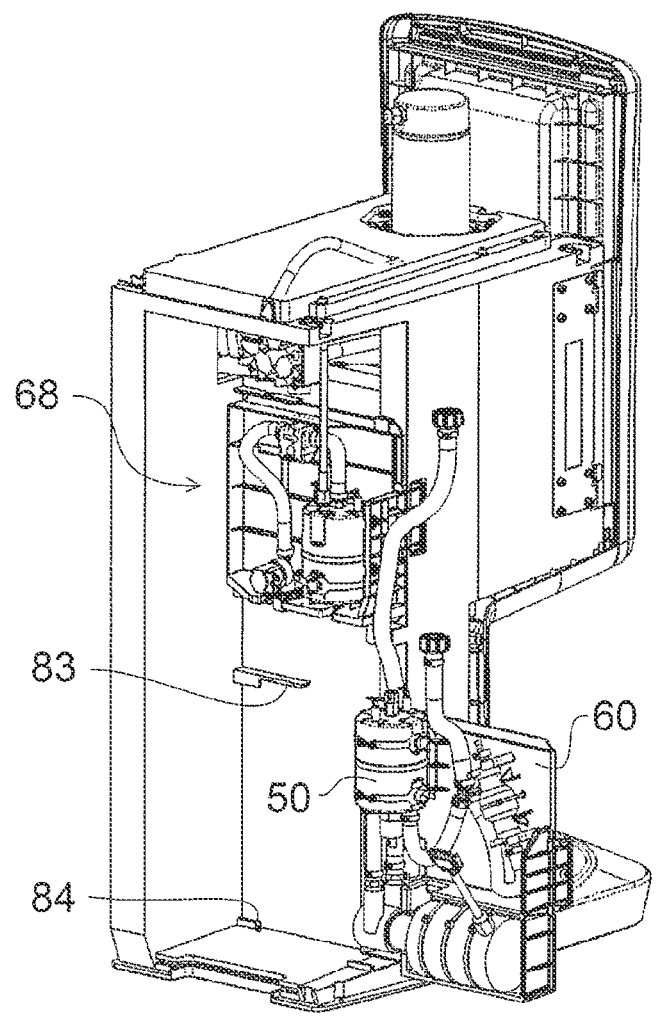
FIG. 7 illustrates the cut-away rear view of the FIG. 5 blender as the water heater assembly tray is being reinserted.
Figure 8:
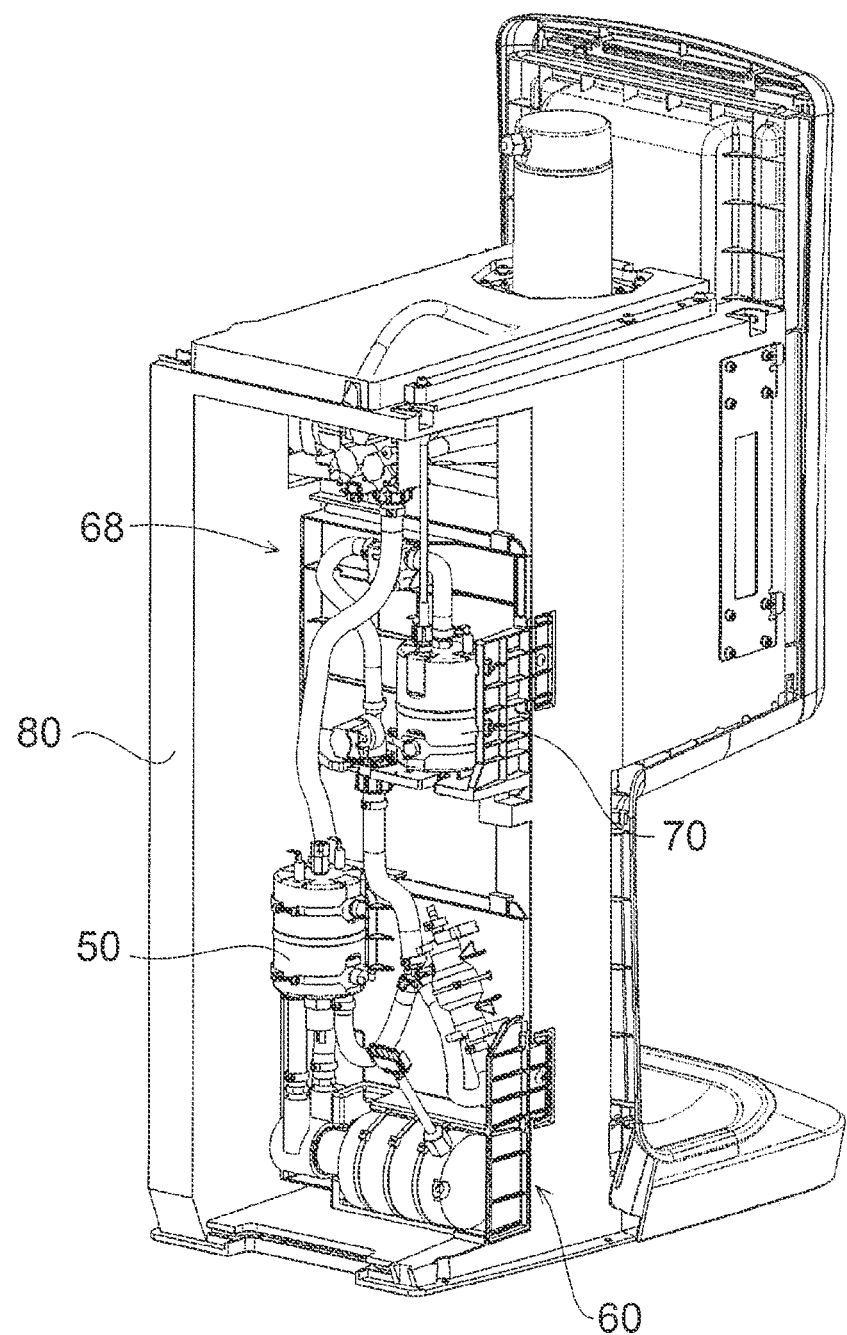
FIG. 8 illustrates the cut-away rear view of the FIG. 5 blender with both the steamer assembly and water heater assembly trays reinserted.

FIG. 5 illustrates the blender 10 of the present invention with both the water heater assembly 60 and steamer assembly 68 removed. With the assemblies 60, 68 removed, slots 81, 82, 83, 84 on the internal frame 80 can be seen. These slots 81, 82, 83, and 84 are for receiving and holding the trays 58, 72 of the assemblies 60, 68. FIG. 6 shows how the steamer tray 72 can be easily inserted into slots 81, 82 on the internal frame 80 to hold the streamer assembly 68 in place. FIG. 7 shows the water heater tray 58 being aligned for insertion into internal frame 80 slots 83, 84. FIG. 8 shows the blender 10 after both the steamer tray 72 and water heater tray 58 have been slid into their respective slots.

Figure 9:
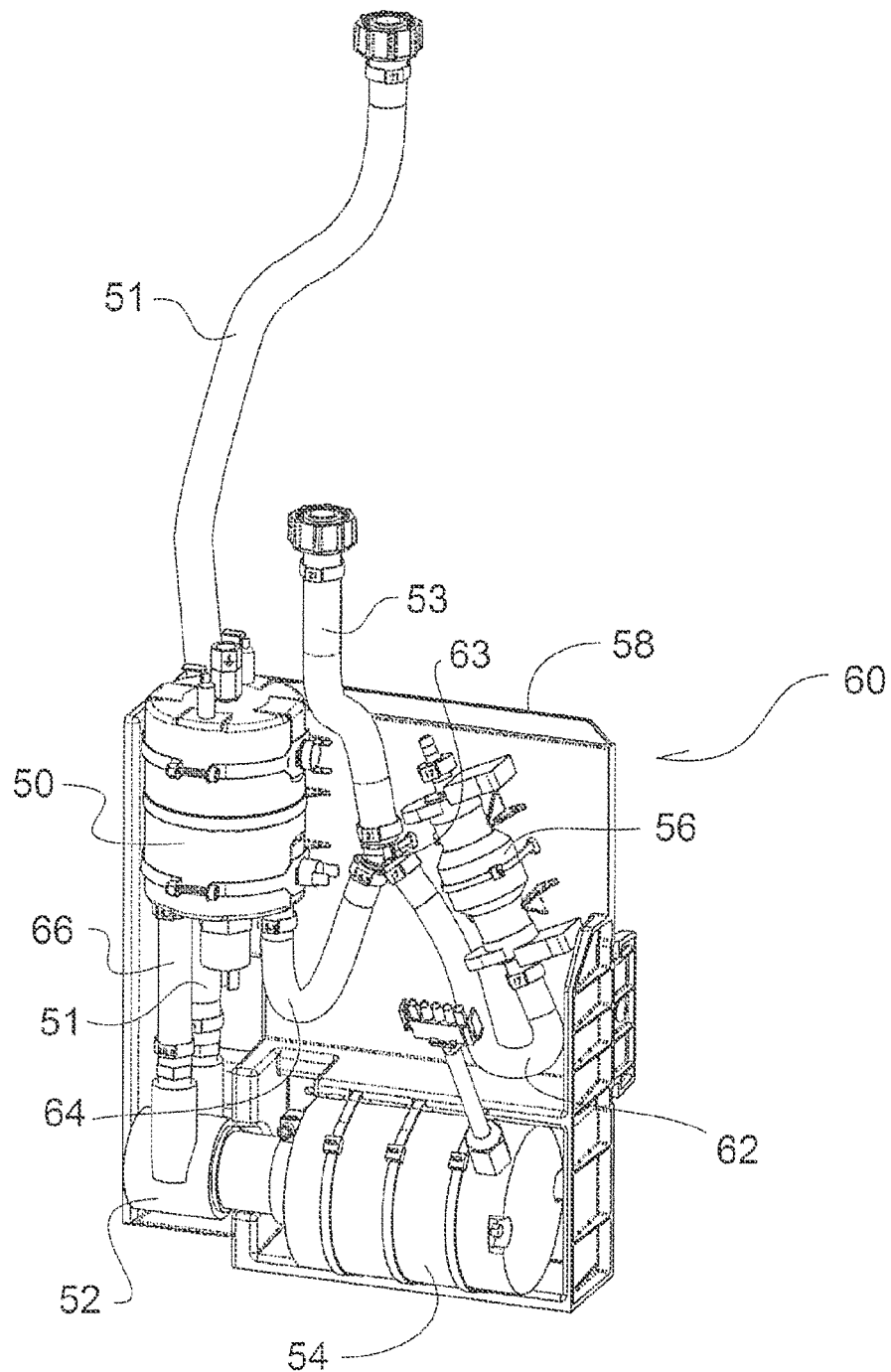
FIG. 9 illustrates a close-up view of the water heater assembly.

FIG. 9 provides a close-up view of the water heater assembly 60 and its components. Referring back to FIG. 4, water preferably comes into the blender 10 from a municipal water supply through water intake hose 59. The intake hose water is first received by pressure regulator 56 in the water heater assembly 60. The pressure regulator 56 caps the water pressure from being too high so that downstream components (e.g., water heater 50 and steamer 70) operate correctly and are not damaged. Preferably, the pressure regulator 56 adjusts the water pressure to below 50 psi. If desired, a water filter can be used in conjunction with the pressure regulator 56 to filter out unwanted particulates and other deposits in the water. From the pressure regulator 56, the water travels through hose 62 to "Y" joint 63 where it goes both to the water heater 50 through water heater intake hose 64 and the steamer assembly 68 through hose 53. To transport heated water to the food preparation chamber 40, the water heater assembly 60 includes a pump 52 and a pump motor 54. When the time comes to rinse the food preparation chamber 40 with hot water, the pump 52 rapidly pulls hot water from the hot water heater 50 through hose 66 and then pumps it through hose 51 until it is sprayed into the food preparation chamber 40 through multiple nozzles, including nozzle 47 (FIG. 3).

Figure 10:
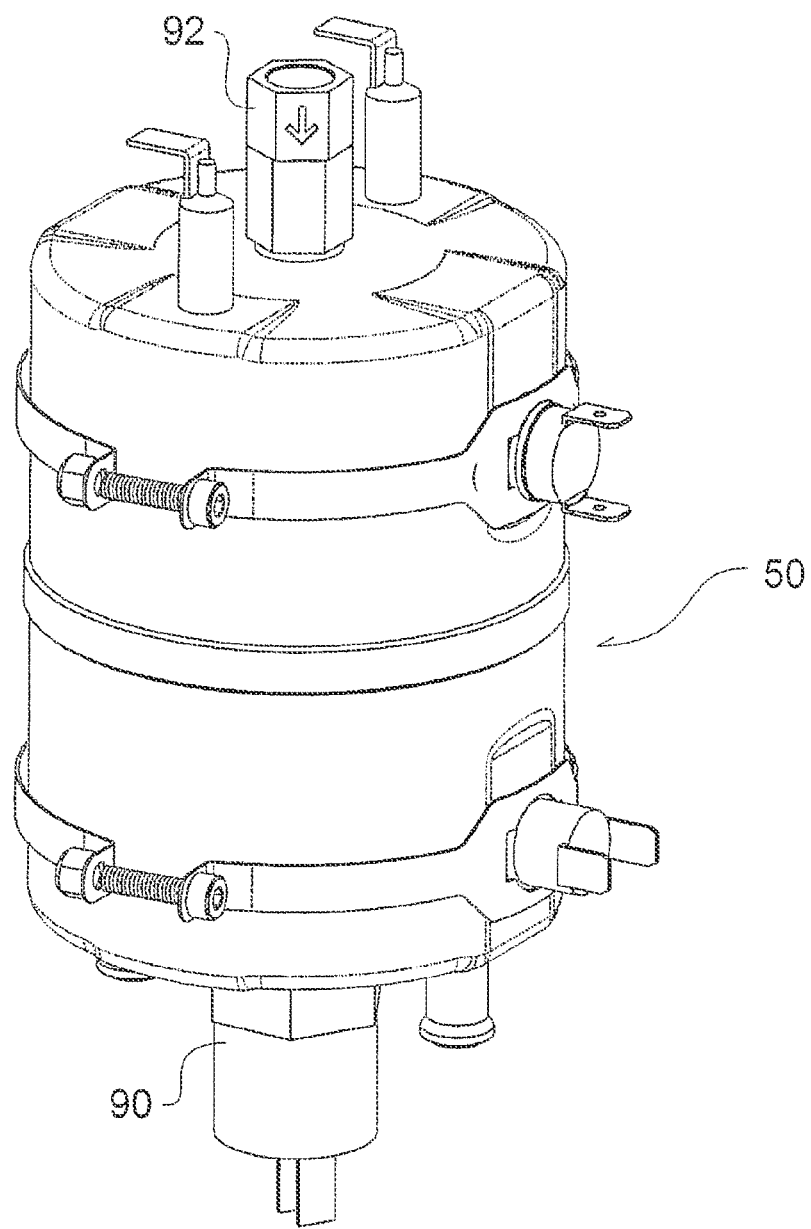
FIG. 10 illustrates a preferred water heater.
Figure 11:
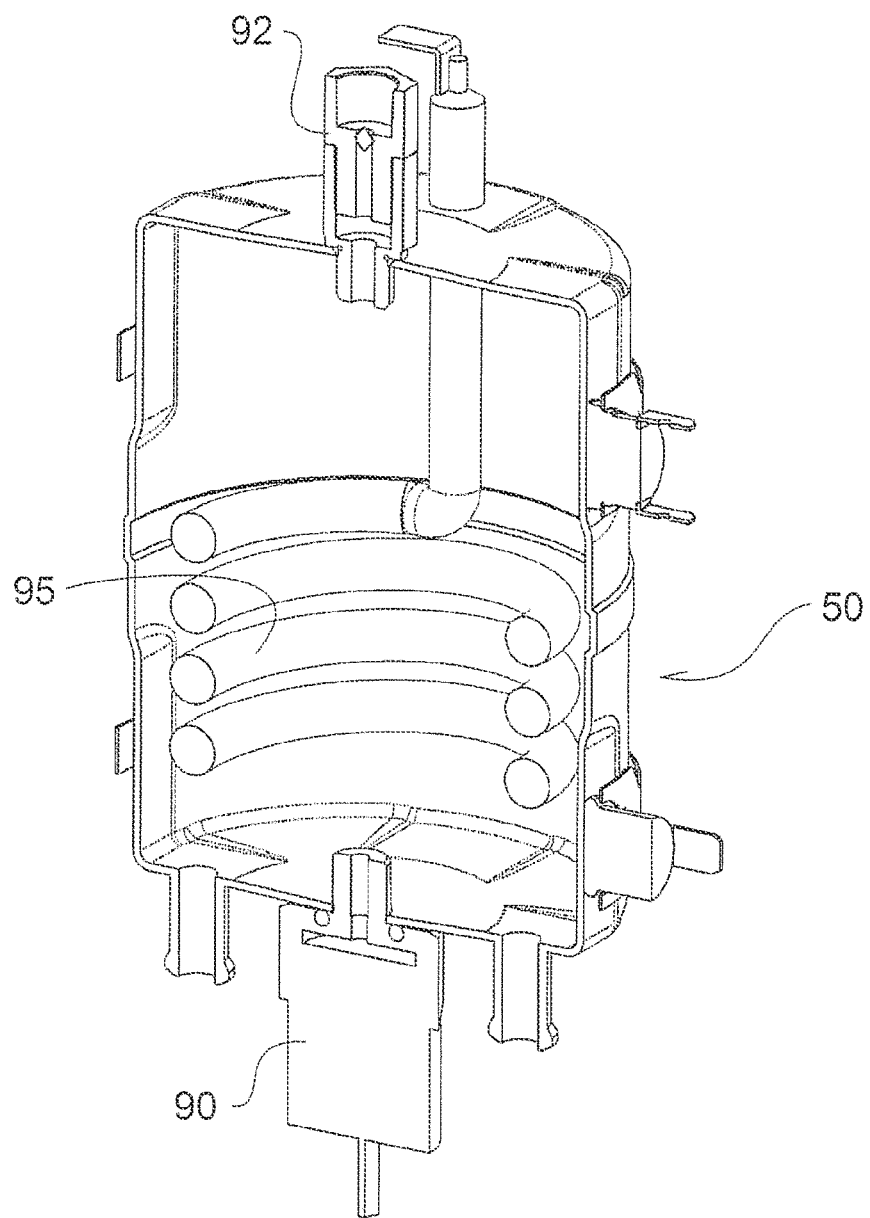
FIG. 11 illustrates a cut-away view of the FIG. 10 water heater.

FIGS. 10-11 illustrate a close-up view of the preferred water heater 50 of the present invention. In previous blenders, a separate water heater and an accumulator with a flexible diaphragm were used to enable a high flow rate of rinse water for the food preparation chamber. In the preferred water heater 50 of the present invention, the water heater 50 and accumulator are combined into a single water heater apparatus 50. As shown in FIG. 11, a heating coil 95 is used to heat the water. In the preferred embodiment, this is an electrical heating coil. To prevent overheating of the heater coil 95, it is important that this heater coil 95 remain primarily immersed in water and not be active when the water heater 50 is empty. This objective is accomplished first by placing the heated portion of the heater coil 95 in the lower portion of the water heater 50 along its inner periphery. In this way, water can be blasted out of the upper portion of the water heater 50 and still leave most of the heater coil 95 immersed in water. To reliably achieve the high flow rate water blast necessary for cleaning the food preparation chamber 40 (and to avoid needing a flexible accumulator diaphragm), a one-way air valve 92 is also provided to allow hot water to be rapidly pumped from the water heater 50 without creating a vacuum resistance. In the preferred embodiment, a pressure activated switch 90 is also provided at the bottom of the water heater 50 to monitor water pressure. If the pressure activated switch 90 measures water pressure to be less than 25 psi, it triggers a shut off of the heating coil 95.

Figure 12A:
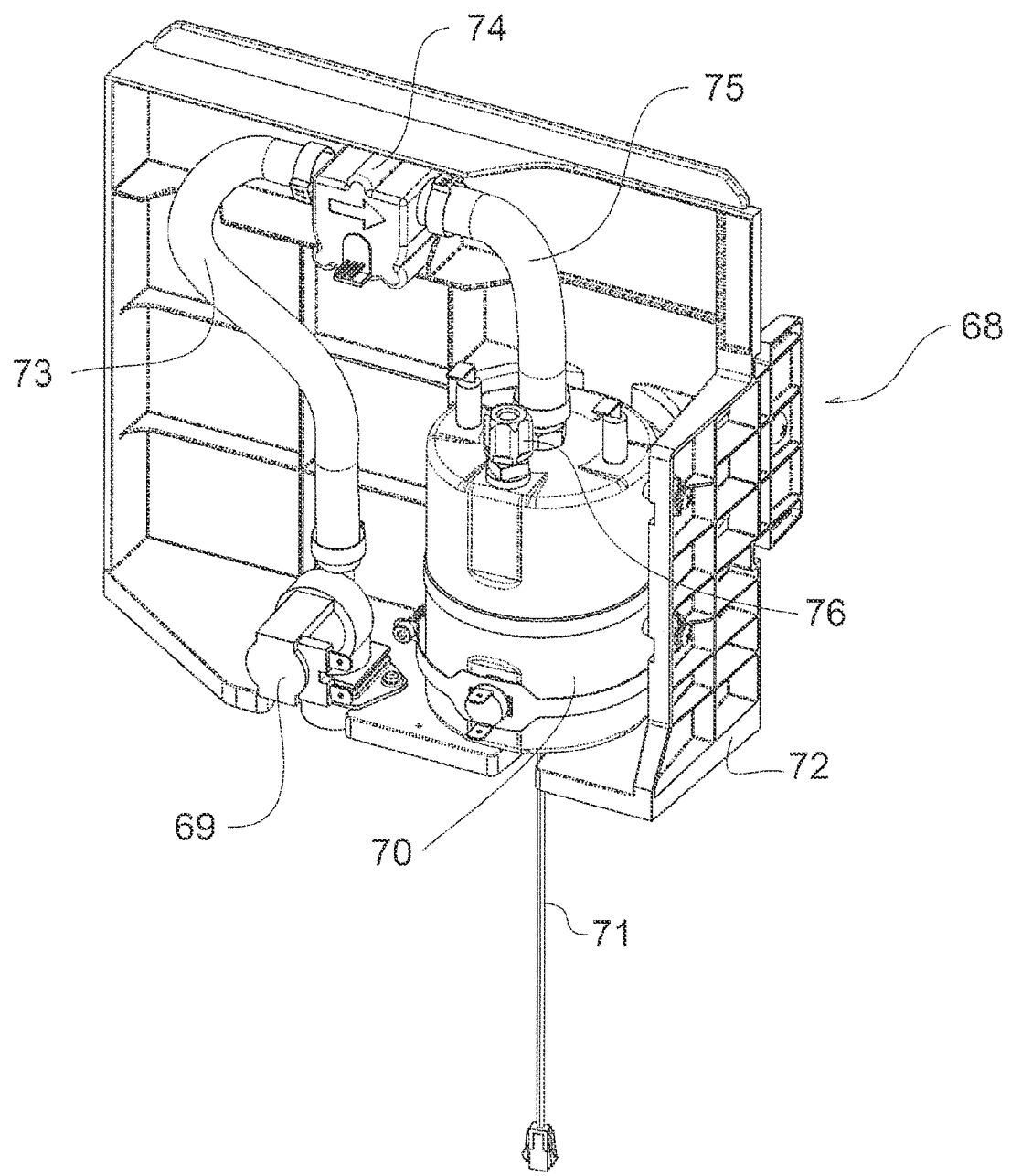
FIG. 12A-C illustrates a close-up view of the steamer assembly and steamer.
Figure 12B:
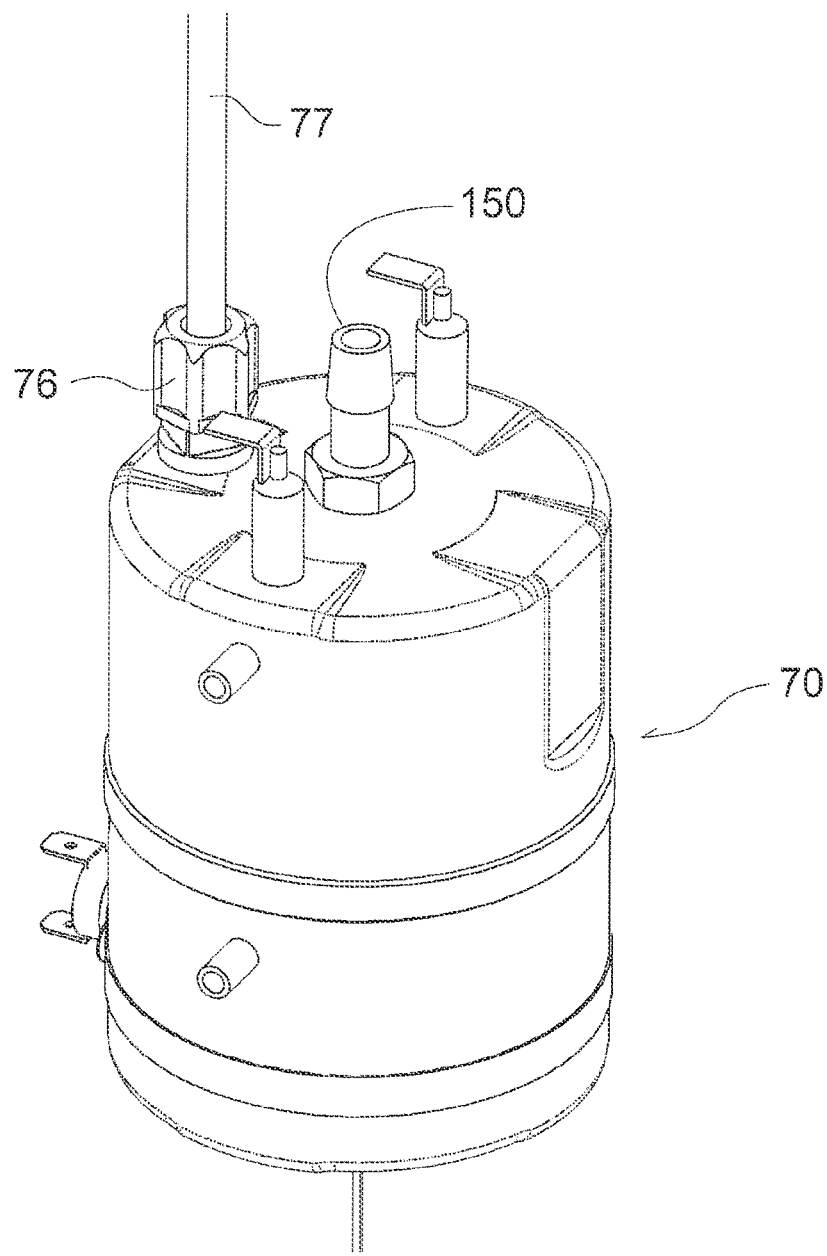
Figure 12C:
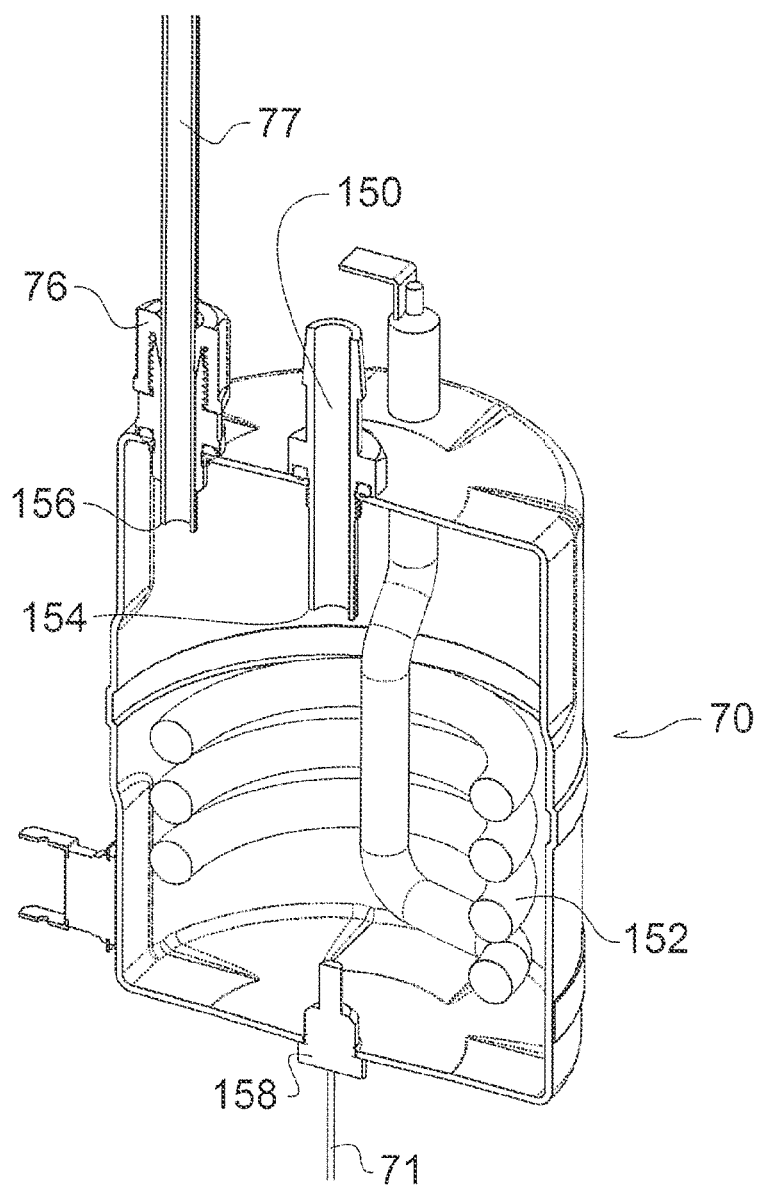

FIG. 12A-C provide close-up views of the steamer assembly 68 and steamer 70 of the present invention. Water enters the steamer assembly 68 through the steamer regulator valve 69. The water is supplied to the steamer regulator valve 69 through a water tube 53, which is part of the water heater assembly 60 (FIG. 9). Water supplied to the steamer regulator valve 69 has passed through the pressure regulator 56, part of the water heater assembly 60 (FIG. 9). Before the water arrives at the steamer 70 through tubes 73, 75, the water first passes through a flowmeter 74. The blender microprocessor (not shown) uses the flowmeter 74 to carefully regulate the amount of water introduced into the steamer 70.

The steamer 70 preferably has two distinct functions. First, it is used to create hot water that can be added in a shot to the food or blended drink. As discussed in f'real's U.S. Pat. No. 5,803,377, adding liquid during the process of blending a frozen milkshake or smoothie is very helpful to achieve a desirable consistency for the blended drink. Second, the steamer 70 supplies steam to clean and sanitize the food preparation chamber 40. Because of the need to control hot water or steam delivery to accomplish these two functions, the steamer regulator valve 69 and flowmeter 74 carefully regulates the amount of water that is allowed to enter the steamer 70 through inlet tube 150 (see, FIG. 12C). The microprocessor turns the steamer regulator valve 69 either on or off and, when on, water flows are regulated at approximately the prescribed rate. Because it is important that water flow to the steamer 70 be done with precision, the flowmeter 74, in its preferred form, has a paddlewheel that accurately measures the amount of water passing through the flowmeter 74 and reports that measurement to the microprocessor. When the exact amount of water needed has passed through the flowmeter 74, the microprocessor turns off the steamer regulator valve 69 to stop further water from flowing into the steamer 70.

The water flow rate that is appropriate for the steamer's first role (adding water to the food or drink) is not appropriate for the steamer's second role (steam cleaning). This is because the steamer 70 must heat the water to a higher temperature for the second role (i.e., to become steam) than for the first role. To allow the same steamer 70 to be used for both roles, the microprocessor opens the steamer assembly's steamer regulator valve 69 for a shorter duration when steam needs to be produced than when hot water needs to be added to the food or drink. In this way, when steam needs to be produced, the steamer regulator valve 69 is not quenching the steam with too much cold water. Temperature readings sent by the temperature sensor 158 through sensor wire 71 are also used by the microprocessor to insure that water/steam sent from the steamer 70 into the food preparation chamber 40 is at the correct temperature.

Referring to the cut-away view of the steamer 70 provided in FIG. 12C, the steamer 70 is preferably a stainless steel vessel with an internal electric heated steamer coil 152 positioned around the inner periphery of the steamer 70. Like the water heater 50 of the present invention, the heated portion of the steamer coil 152 is preferably placed in the lower portion of the steamer 70. In this way, overheating of the steamer coil 152 can be avoided by keeping the steamer coil 152 primarily immersed in water and not active when the steamer 70 is empty. Preferably, water must be added while steam is being generated to ensure the steamer coil 152 does not operate while dry.

At the top of the steamer 70 is a water inlet tube 150 with a down tube portion 154. To avoid quenching the steam with cold water, it is desirable that the down tube portion 154 of the water inlet tube 150 deposit intake water near the bottom of the vessel. Nonetheless, if the down tube portion 154 is so long that it deposits incoming water on the temperature sensor 158, the temperature sensor 158 will not provide accurate temperature readings to the microprocessor. To overcome this problem of selecting an appropriate length and placement for the down tube portion 154, the inventors discovered that a toroidal vortex of hot water is created by the boiling convection of the peripheral heating coil 152 in the steamer 70. Due to this vortex, as long as the down tube portion 154 is located at the center of the vortex, the down tube portion 154 can be relatively short, in some cases on the order of ¾ of an inch, and still deposit incoming water to the bottom of the vessel (i.e., through the middle of the vortex) avoiding quenching the boiling while allowing sufficient mixing to avoid chilling the temperature sensor 158. To further insure that steam, rather than cold water, is being conveyed to the food preparation chamber 40 for sanitation, the lower end of the steam outlet tube 77 should be higher than the lower end of the down tube portion 154 of the water inlet tube 150. The inventors have found that, in one preferred embodiment, this height difference can be on the order of ½ inch.

Figure 13:
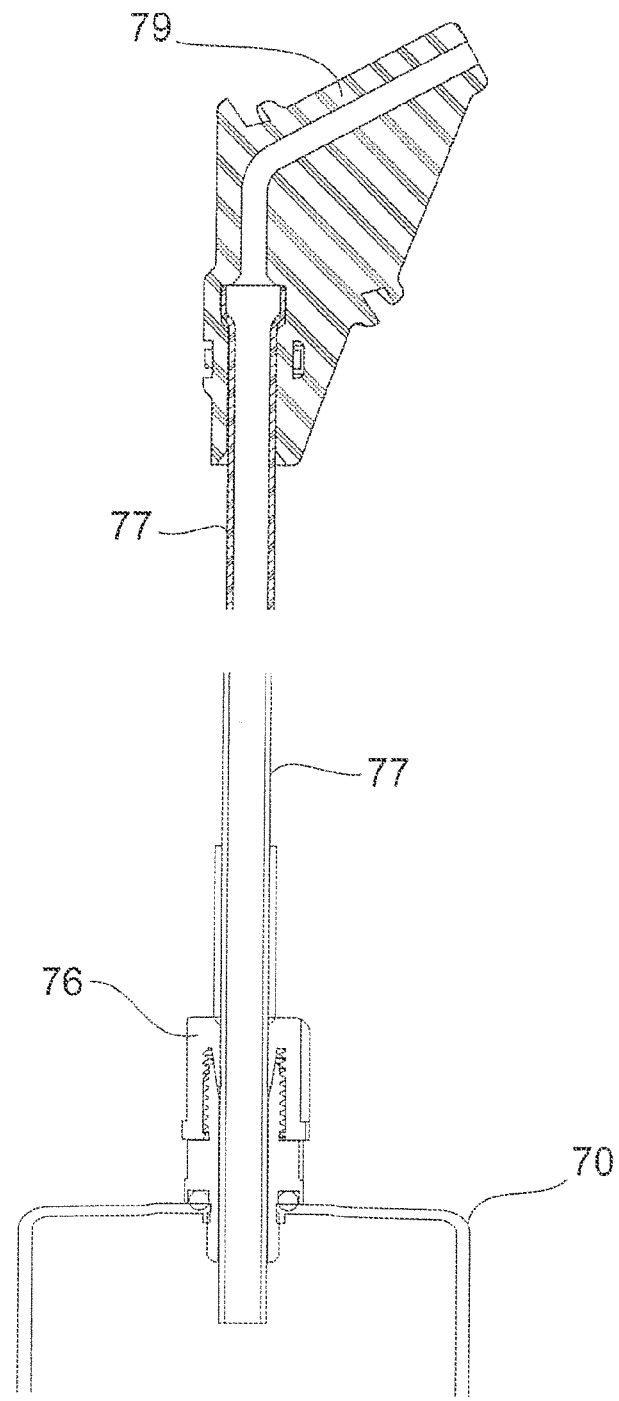
FIG. 13 illustrates the tubing connection between the steamer and the food preparation chamber.

FIG. 13 illustrates an important advance in transporting steam from the steamer 70 to the food preparation chamber 40. It is common that there are dissolved solids in the steam feed water. When boiling occurs in the steamer, these dissolved solids will tend to precipitate and build up on most surfaces in contact with the boiling water and steam. These precipitated solids are commonly referred to as scale. In previous blenders, scale build up in constricted flow paths, such as the steamer tubing and fittings, would cause reliability issues. When such components became clogged with scale, they needed to be repaired or replaced. To minimize maintenance, a seamless non-stick tube 77 made from a lubricious (i.e., non-stick) material, such as polytetrafluoroethylene (PTFE)—commonly known as TEFLON™, is preferably used as a steamer outlet to transport steam from the steamer 70 to the food preparation chamber 40. Alternative lubricious (i.e., non-stick) materials include ethylene tetrafluoroethylene (ETFE), ethylene chlorotrifluoroethylene (ECTFE), polychlorotrifluoroethene (PCTFE), fluorinated ethylene propylene (FEP), perfluoroalkoxy (alkane) (PFA), poly (tetrafluoroethylene+perfluoromethylvinyl ether) (MFA) and polyvinylidene fluoride (PVDF). Due to the non-stick qualities of these materials, the inventors have found that scale does not build up on these tubes the way scale deposits on less lubricious tubes. While this seamless non-stick tube 77 may be connected to the steamer by a fitting 76, the seamless non-stick tube 77 is preferably fully inserted into the steamer 70 so that there is no contact between the steam and any non-lubricious material. Similarly, the seamless non-stick tube 77 should extend into the food preparation chamber 40 in a way that avoids steam contact with any non-lubricious material. The steam nozzle 79, if used, is also preferably made from PTFE or another lubricious material. Alternatively, it can be fabricated from flexible high temperature materials, such as silicone rubber. To the extent scale sticks to flexible material, it can be dislodged by simply flexing the steam nozzle 79.

Figure 14:
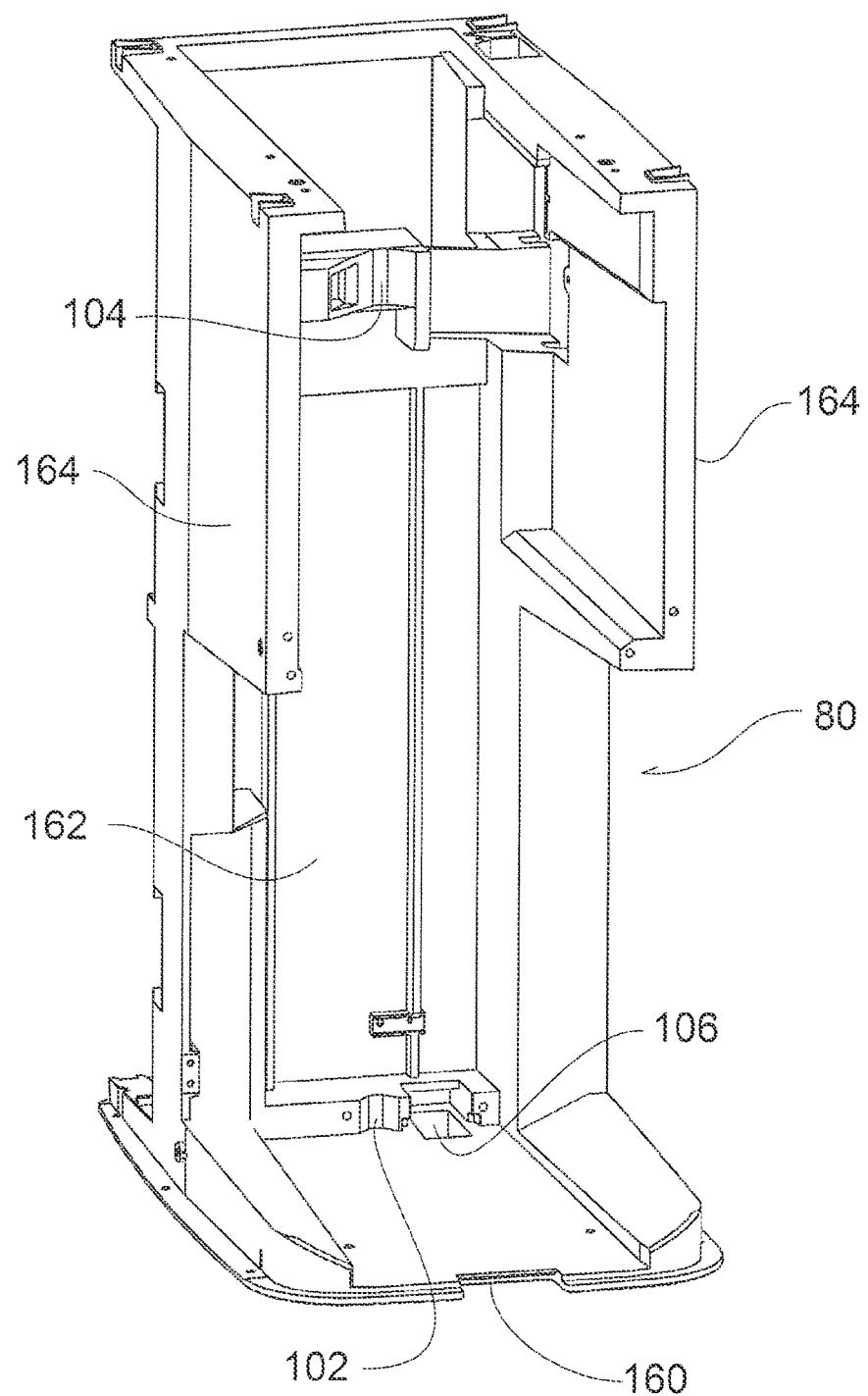
FIG. 14 illustrates the preferred internal frame.

FIG. 14 illustrates a preferred form of internal frame 80 for the blender 10 of the present invention. In this preferred embodiment, the internal frame 80 is of single piece construction with a horizontal base 160, a vertical plate 162 rising up from the base 160 and two arms 164 extending forward from the upper portion of the vertical plate 162. As those of skill in the art will recognize, the internal frame 80 could alternatively be made from multiple pieces and in different shapes.

One of the challenges in lowering blender costs for both the manufacturer and user is making the blender 10 easy to assemble and maintain. The internal frame 80 of the present invention allows key components of the blender 10 to be either slid, snapped or easily assembled into place on a centrally located support structure. As shown in FIGS. 5-8, the trays 58, 72 for the water heater assembly 60 and steamer assembly 68 can be slid into the internal frame 80 easily and quickly to place them in their exact positions. As illustrated in FIGS. 15-21, the components of the cupholder elevator assembly 30 can be exactly aligned and snapped into place on the front side of the internal frame 80 with little effort. As shown in FIGS. 1-4, the internal frame 80 also serves as a support for the mix motor assembly 44, food preparation chamber 40, optional video screen 14, control panel 16 and external housing 12. While not illustrated in the drawings, the internal frame 80 additionally supports the blender's electronics, including the blender's microprocessor.

The internal frame 80 of the present invention is preferably injection molded from a hard, durable thermoplastic, such as NORYL™ resins. NORYL™ resins are amorphous blends of polyphenylene ether resins and polystyrene. By serving as a multi-purpose base that allows the key components of the blender 10 to be precisely aligned and held in place, the internal frame 80 eliminates much of the assembly alignment work in blender manufacture and eliminates the need for a multiplicity of parts to connect all of the key blender components together.

Figure 15:
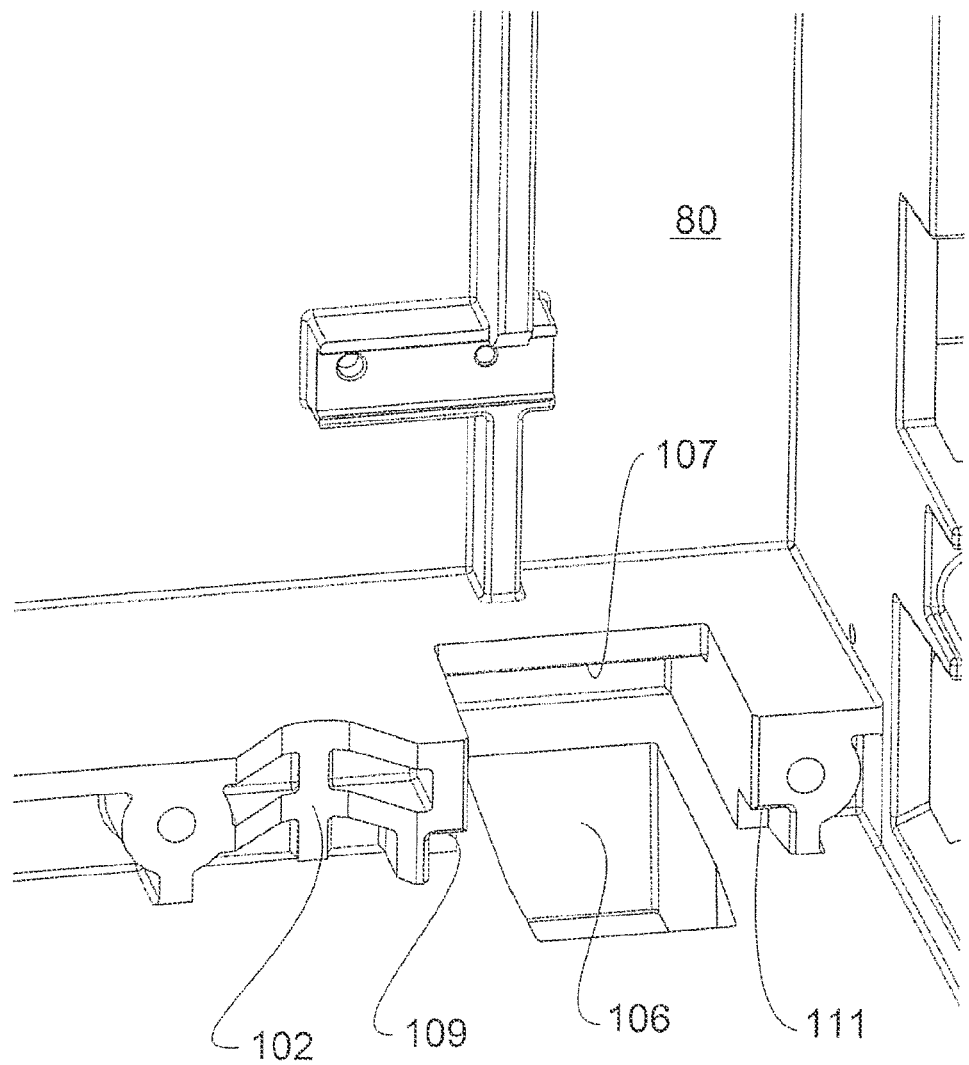
FIG. 15 illustrates the lower portion of the FIG. 14 internal frame that receives the cupholder elevator assembly.
Figure 16:
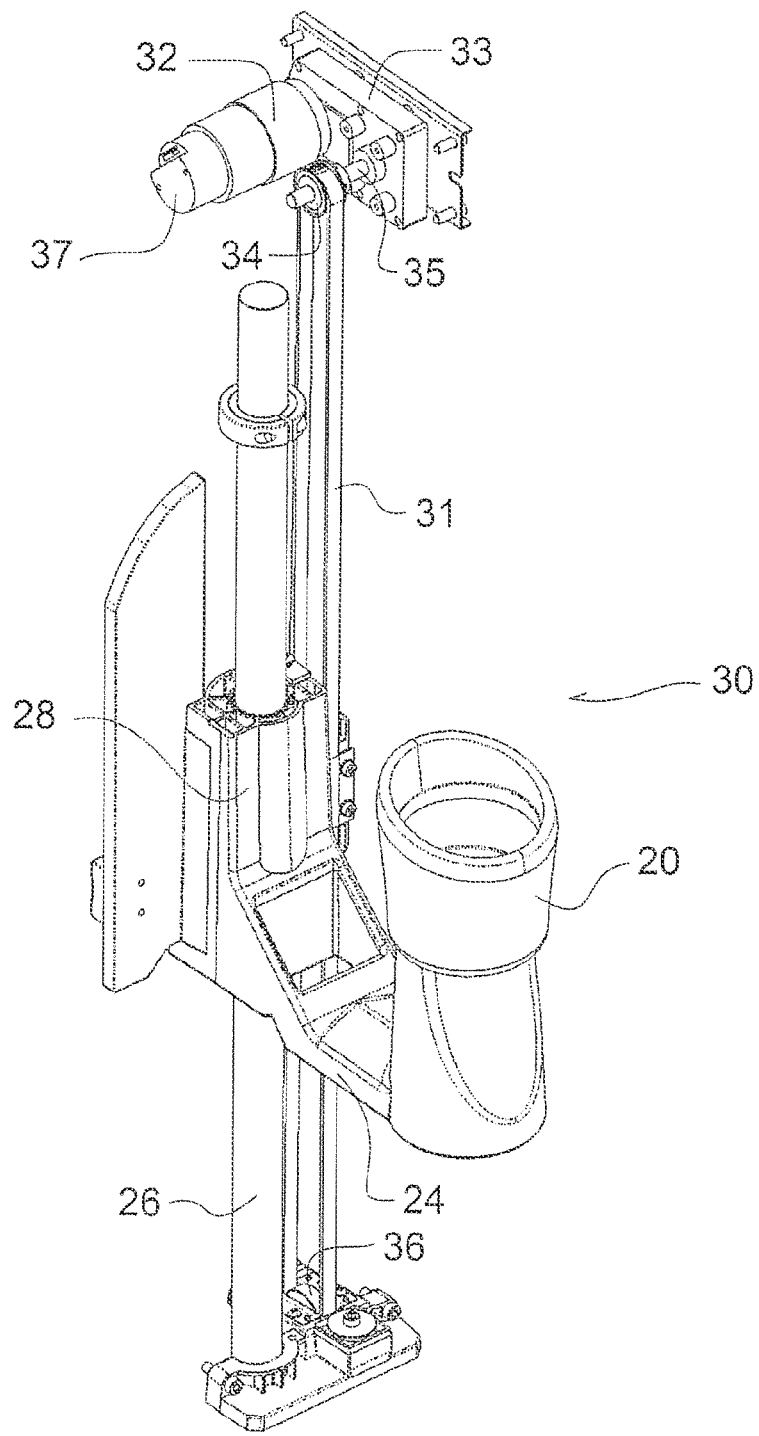
FIG. 16 illustrates a preferred form of belt-driven cupholder elevator assembly.
Figure 17:
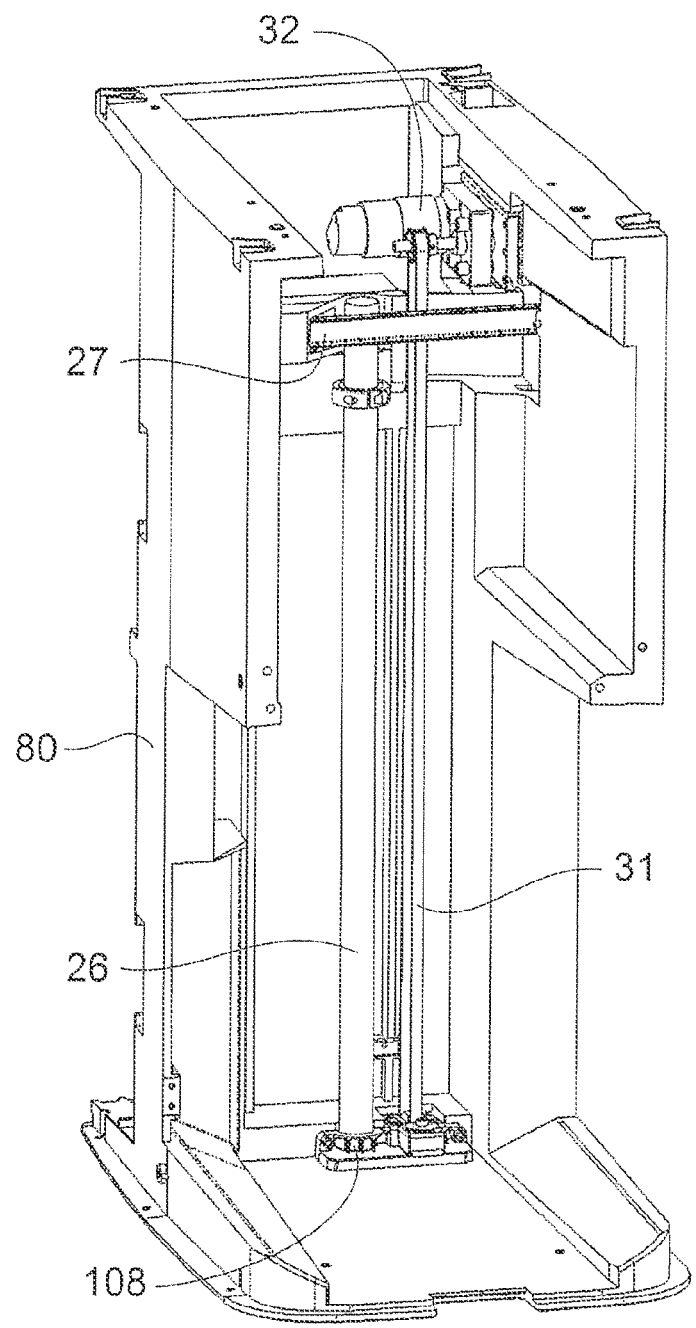
FIG. 17 illustrates how the preferred belt-driven cupholder elevator assembly attaches into the FIG. 14 internal frame.
Figure 18A:
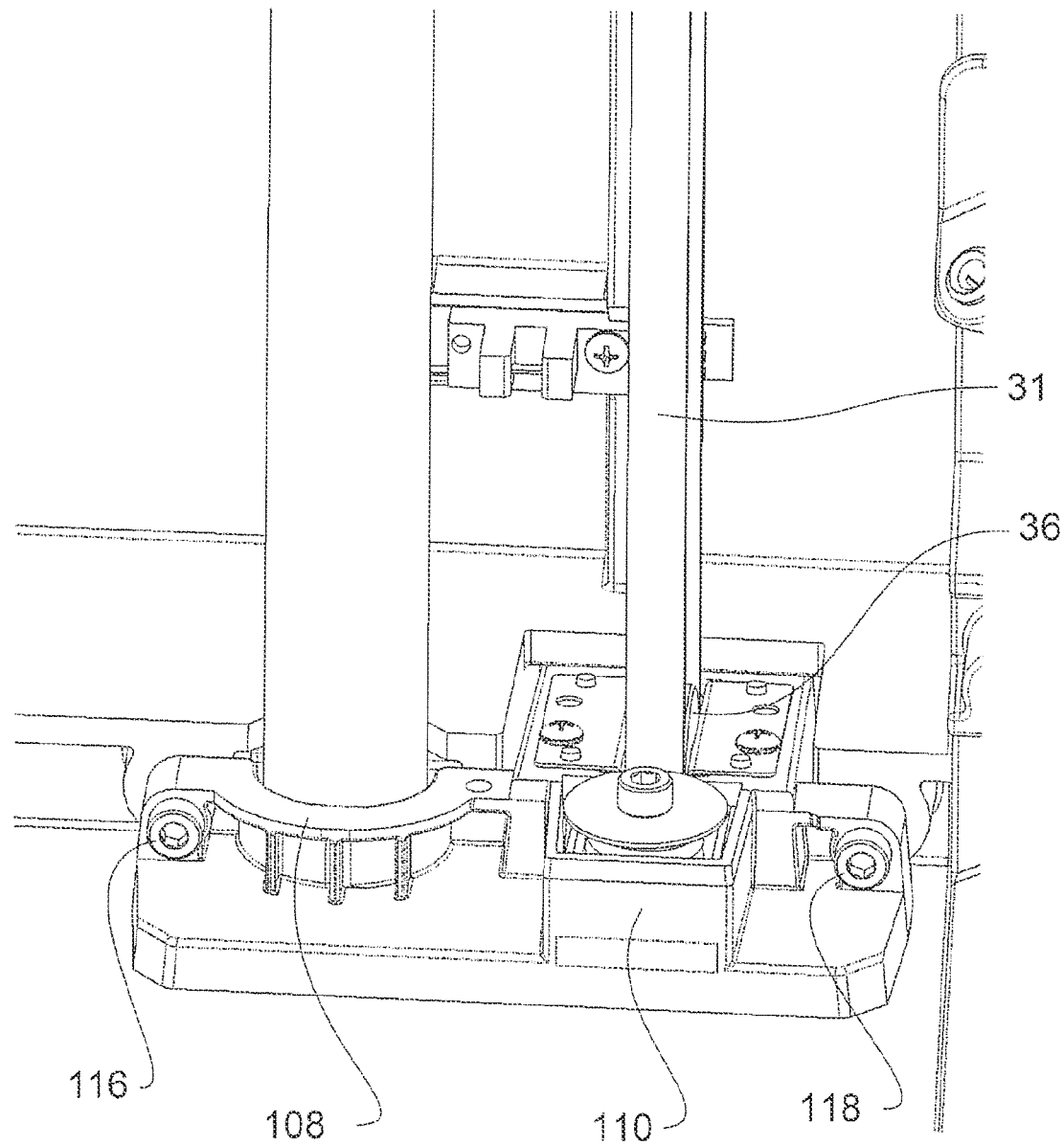
FIGS. 18A-B illustrate lower close-up views of how the belt-driven cupholder elevator assembly attaches into the internal frame.
Figure 18B:
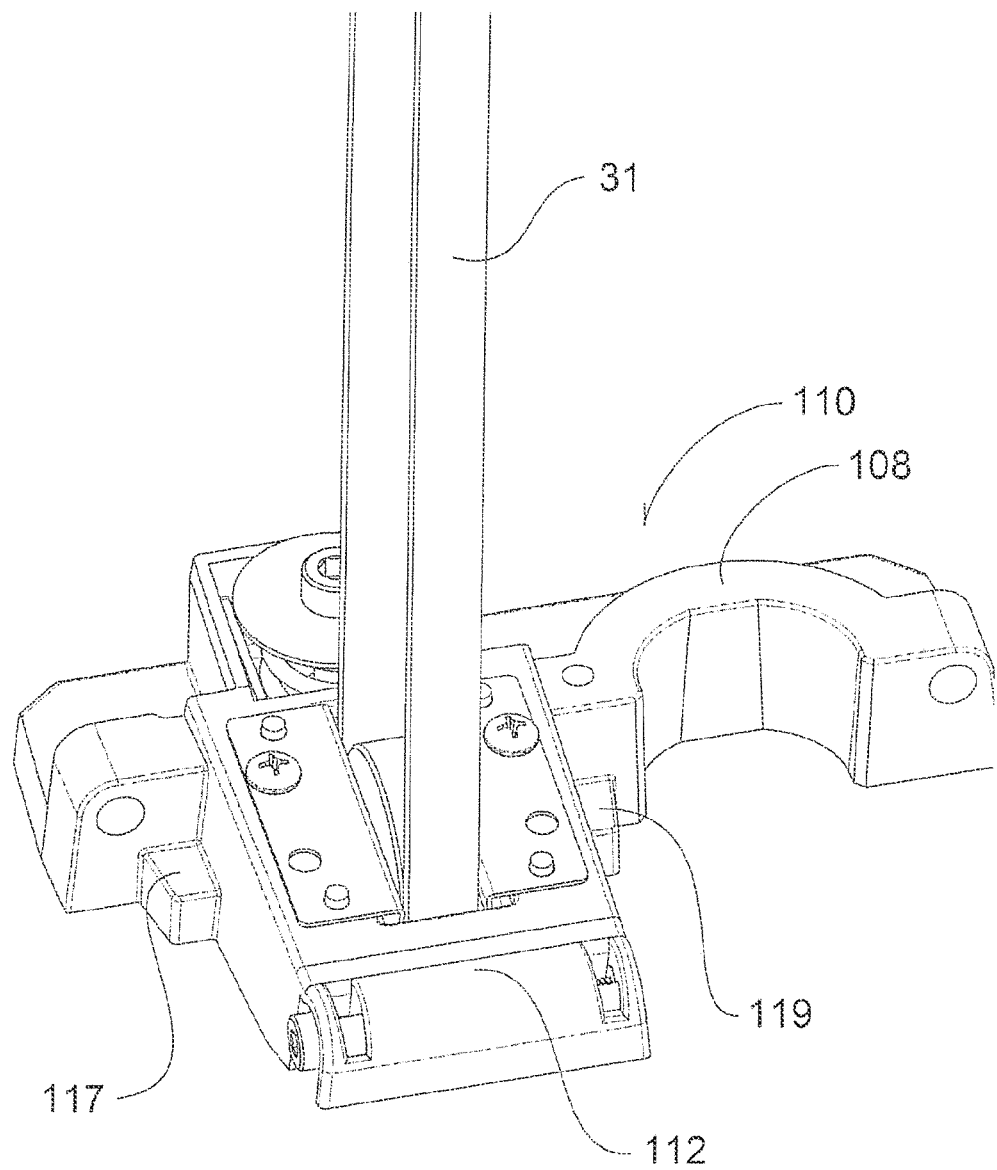

As shown in FIGS. 14-15, the internal frame 80 uses lower groove 102, upper groove 104 and lower receiving port 106 in its preferred embodiment to attach the cupholder elevator assembly 30. As shown in FIG. 16, the cupholder elevator assembly 30 includes cupholder 20, cantilevered cupholder connector 24, sliding cupholder traveler 28, guide rod 26, drive belt 31, drive motor 32, gear box 33, drive shaft 35, encoder 37, drive pulley 34 and idler roller 36. Through its connection to the sliding cupholder traveler 28, the drive belt 31 is used to move the cupholder 20 up and down. Under the control of the microprocessor (not shown), the drive belt 31 is powered by drive motor 32 acting through gear box 33, drive shaft 35 and drive pulley 34. While a drive belt 31 is used to transport the cupholder 20 in the preferred embodiment, one or more lead screws could alternatively be used in the cupholder elevator assembly 30 as described in f'real's U.S. Pat. No. 9,420,917. Likewise, multiple drive belts could alternatively be used.

For manufacture, the challenge is to attach the cupholder elevator assembly 30 to the internal frame 80 as quickly, easily and accurately as possible. For the guide rod 26, this is simply a matter of first pushing the upper and lower ends of the guide rod 26 into the backs of the lower groove 102 and upper groove 104. The lower 102 and upper 104 grooves are preferably curved in a "U" shape or have two angled faces forming shallow "V" shape to accurately seat and secure the guide rod 26. An upper guide rod clamp 27 and lower guide rod clamp 108 (part of the spring-biased idler assembly 110 shown in FIG. 18B) are then used to lock the upper and lower ends of the guide rod 26 in place (see, FIG. 17).

Attaching the drive belt 31 and idler roller 36 to the internal frame 80 requires a little more effort. To work correctly, the drive belt 31 must be properly tensioned. Again, to maximize quality and save cost, it is desirable that this proper tensioning be done accurately, quickly and easily. In the preferred embodiment, fixed locations on the internal frame 80 are provided for the drive motor 32, gear box 33, drive shaft 35 and, by extension, the drive pulley 34. That leaves the challenge of how to position the idler roller 36 and drive belt 31.

Figure 19:
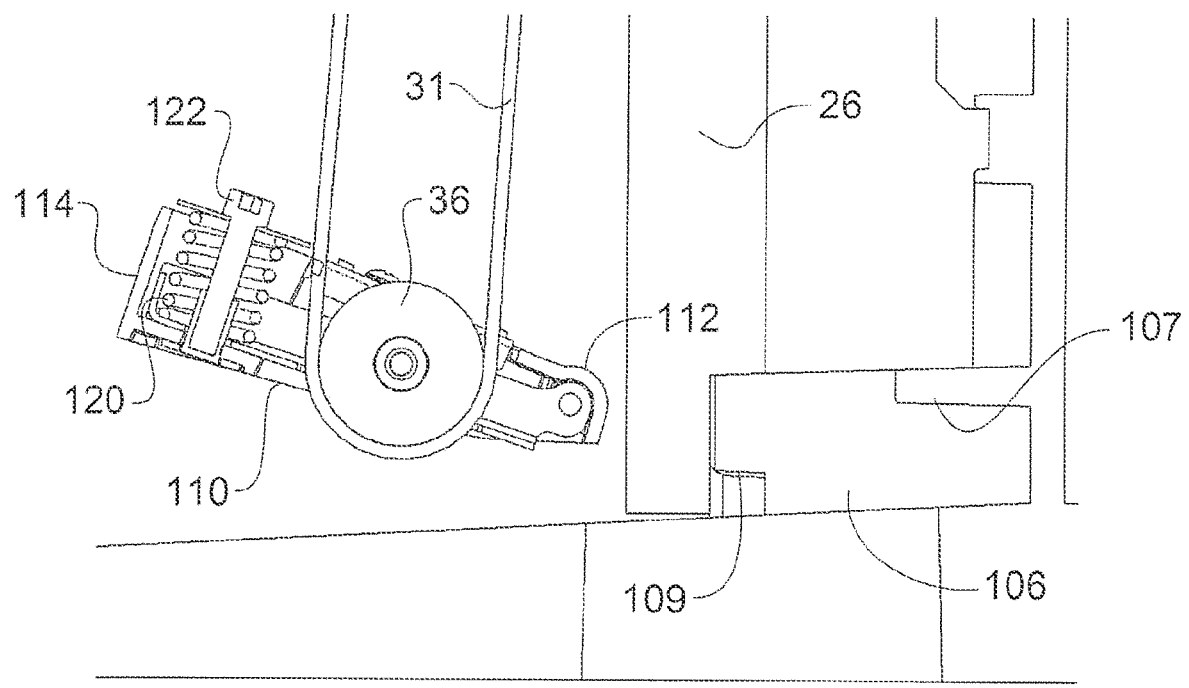
FIG. 19 illustrates how a drive belt idler assembly of the cupholder elevator assembly can be aligned for insertion into a lower receiving port of the internal frame.
Figure 20:
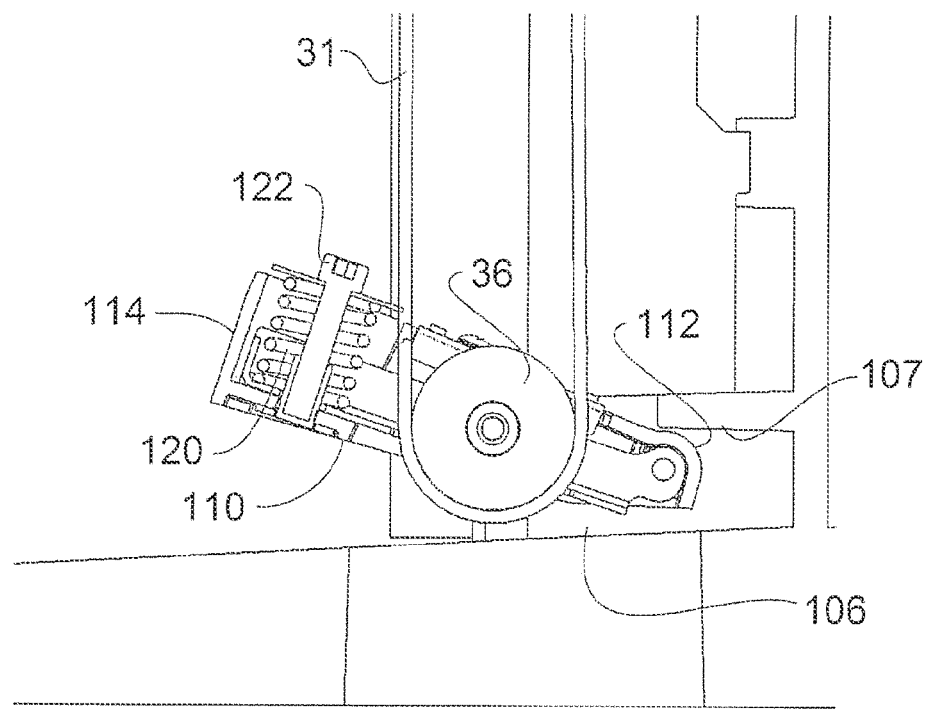
FIG. 20 illustrates insertion of the toe of the drive belt idler assembly of FIG. 19 into the lower receiving port of the internal frame.
Figure 21:
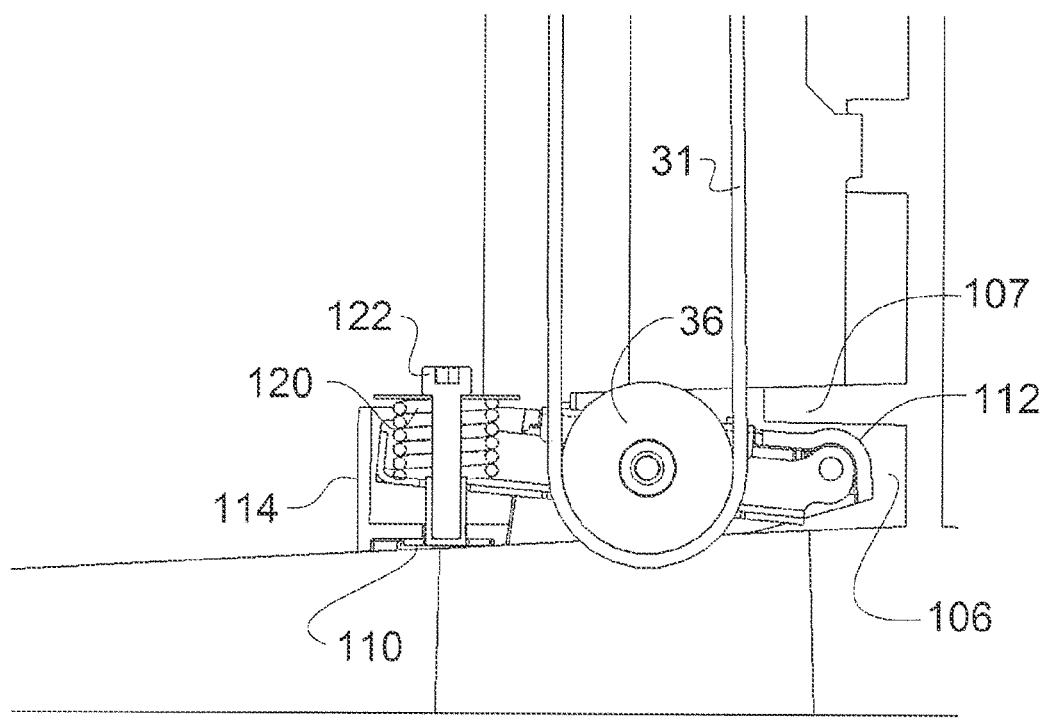
FIG. 21 illustrates attachment of the FIG. 19 drive belt idler heel onto the internal frame.

In the present invention, the drive belt installation problem is solved through use of a spring-biased idler assembly 110 in cooperation with the lower receiving port 106 on the internal frame 80. As shown in FIGS. 18A-FIG. 21, the drive belt 31 is preferably attached at one end to the fixed drive pulley 34 during installation and attached at the other end to the idler roller 36 of the spring-biased idler assembly 110. After being so attached, the toe 112 of the spring-biased idler assembly 110 is moved toward the lower receiving port 106 of the internal frame 80 as shown in FIG. 19. The lower receiving port 106 preferably has a ledge 107. As shown in FIG. 20, the toe 112 of the spring-biased idler assembly 110 slides under the ledge 107 of the lower receiving port 106. After the toe 112 is fully inserted under the ledge 107, the spring-biased idler assembly 110 is lowered into a horizontal position so that its heel 114 is placed in contact with the internal frame 80 (FIG. 21). Next, the spring-biased idler assembly 110 is moved further into the lower receiving port 106 so the idler heel tabs 117, 119 (see, FIG. 18B) are inserted into tab slots 109, 111 in the internal frame 80 (see, FIG. 15). Idler screws 116, 118 (FIG. 18A) are then used to secure the spring-biased idler assembly 110 and guide rod 26 to the internal frame 80. The spring-biased idler assembly 110 has an idler spring 120 placed around idler spring screw 122 which makes sure that the drive belt 31 is set to the proper tension.

Figure 22:
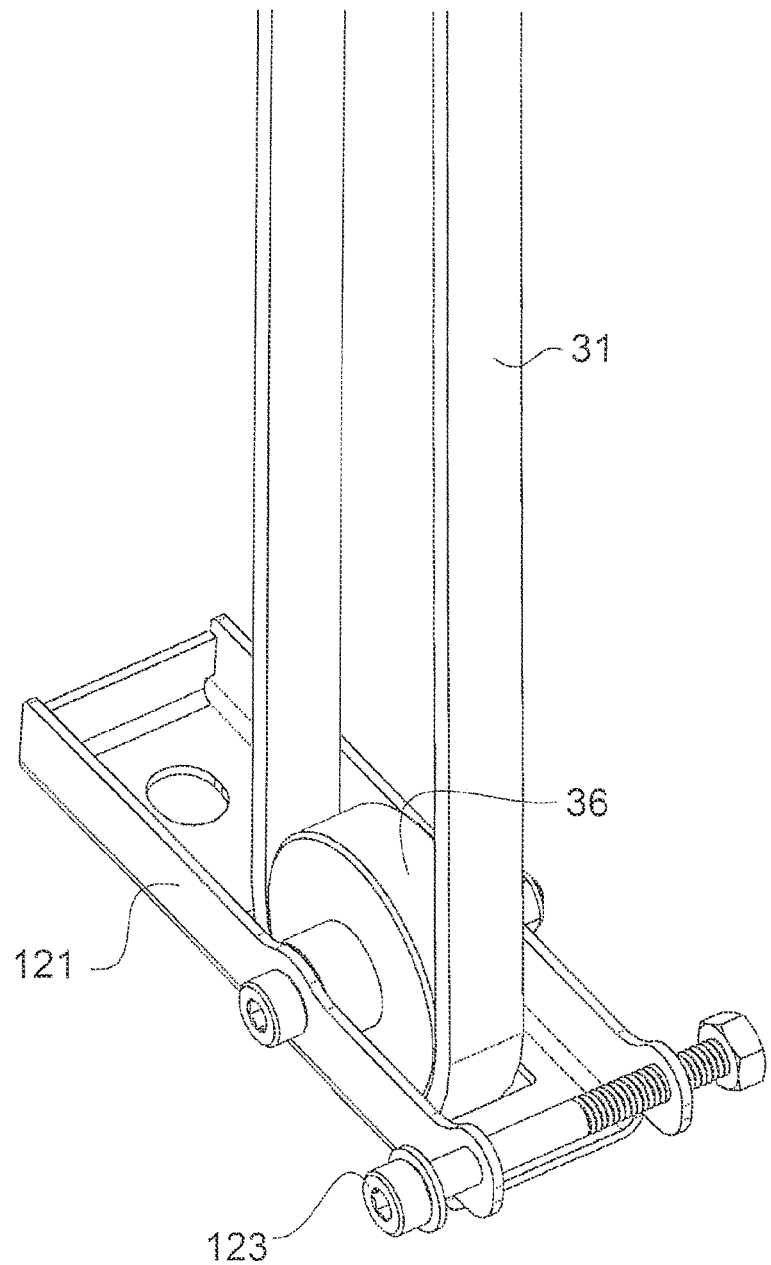
FIG. 22 illustrates the idler roller portion of the preferred drive belt idler assembly.
Figure 23:
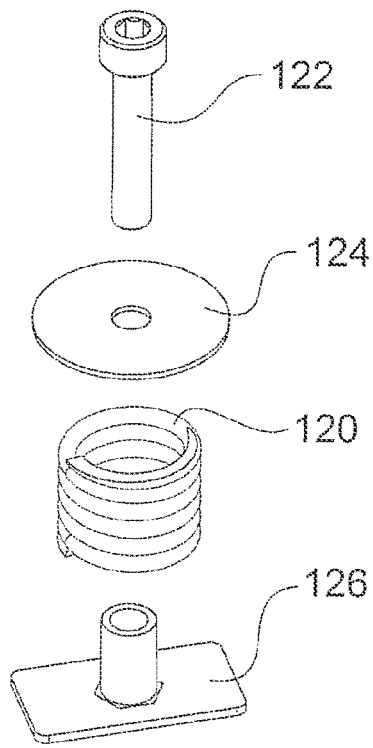
FIG. 23 illustrates the spring biasing portion of the preferred drive belt idler assembly.

FIGS. 22-23 provides a close-up view of the parts of the spring-biased idler assembly 110. FIG. 22 illustrates the idler roller 36, idler pivot plate 121, an idler pivot bolt 123 and drive belt 31. FIG. 23 illustrates the idler spring 120, idler spring screw 122, idler spring washer 124 and idler spring nut 126 to receive the idler spring screw 122.

Figure 24:
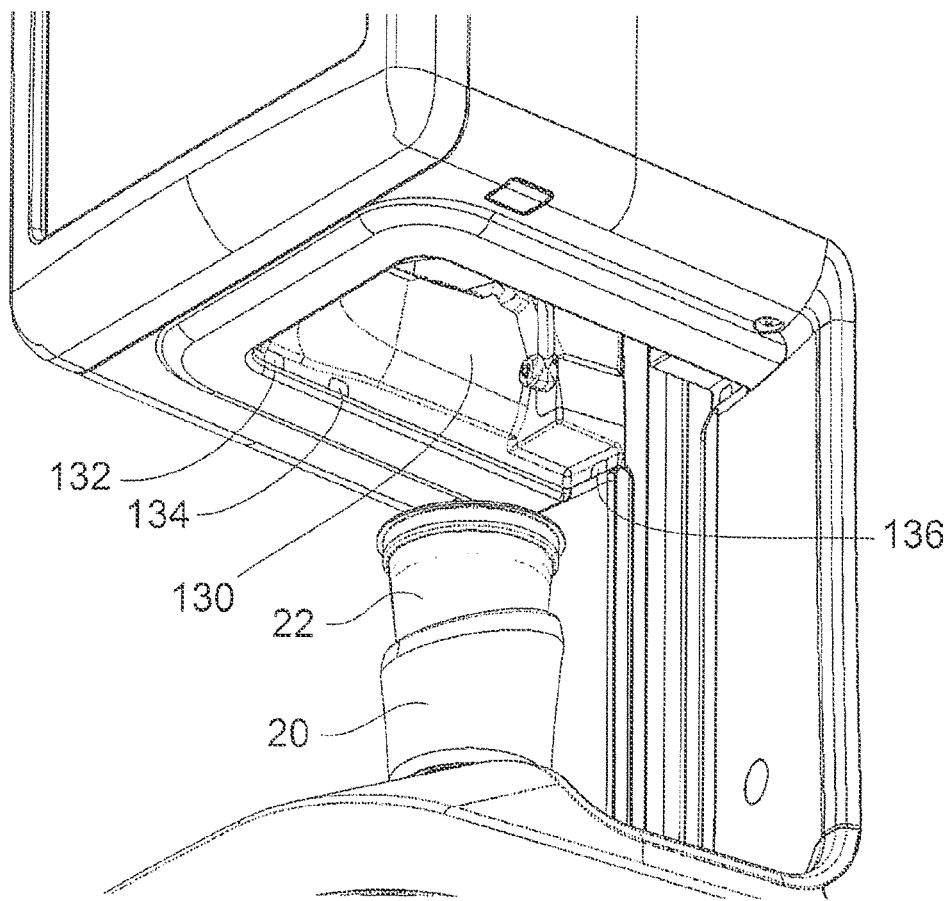
FIG. 24 illustrates the cupholder being raised into the entrance of the food preparation chamber.
Figure 25:
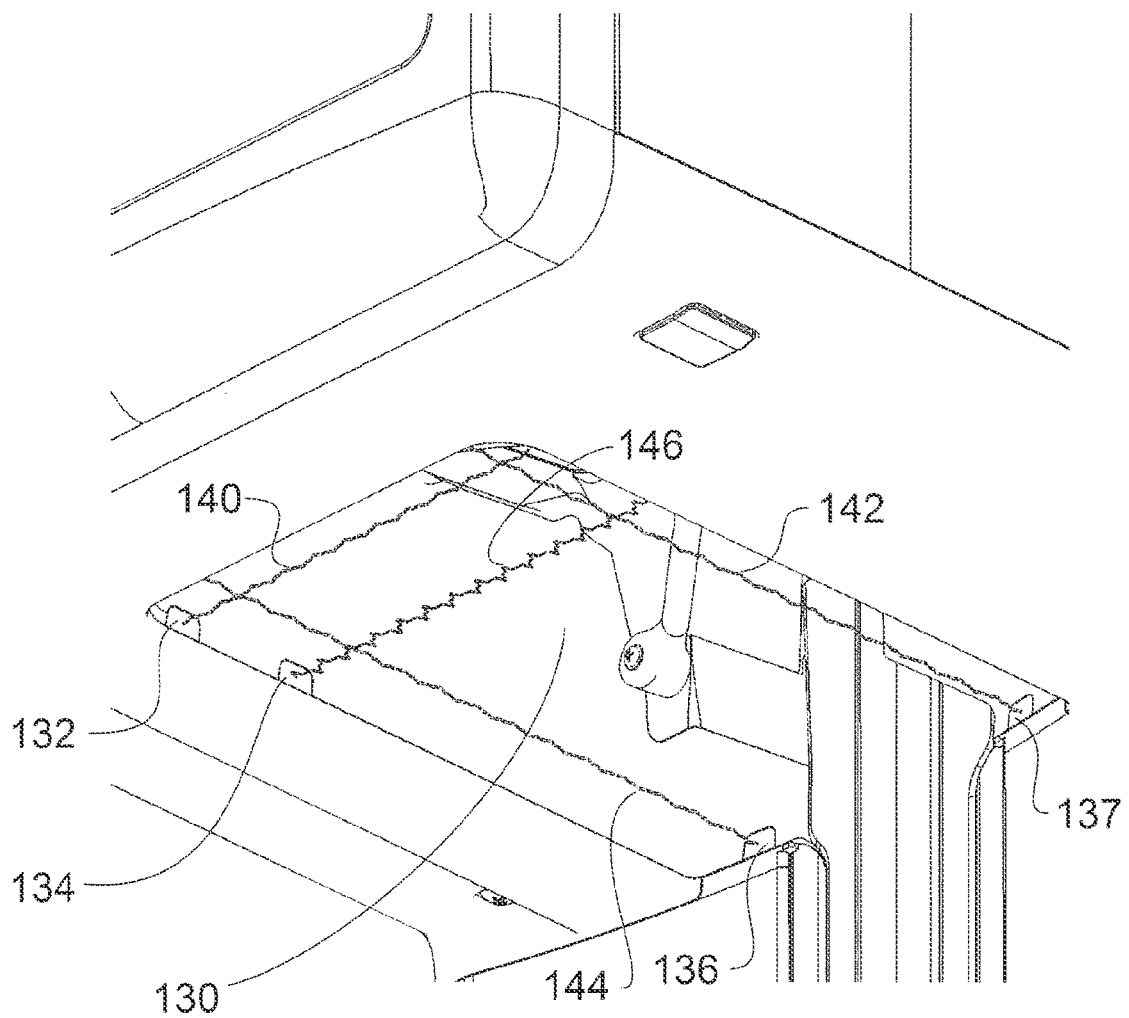
FIG. 25 illustrates crisscrossing light beams at the entrance of the food preparation chamber.

FIGS. 24-25 illustrate the use of safety light beams 140, 142, 144 and the cup size light beam 146 at the entrance 130 of the food preparation chamber 40 to insure that the blender 10 of the present invention is used safely. Each light beam is created by an emitter 132, 134, 136, 137 and detected by a sensor (not shown). As recognized by those of skill in the art, the position of the emitters 132, 134, 136, 137 and sensors can be interchanged with the objective or minimizing cross-talk between the beams and interference from other sources. The light beams are preferably infrared light beams but, as those of skill in the art will recognize, other types of light beams could also be used. In the preferred embodiment shown in FIGS. 24-25, the cup size light beam 146 is used to determine whether a cup 22 of appropriate size has been correctly placed in the cupholder 20 while the other three safety light beams 140, 142, 144 are used to detect whether a foreign object, such as a customer's hand, is below the food preparation chamber.

In the preferred embodiment, the blender 10 of the present invention is optimized to blend frozen milkshakes and smoothies in particular size cups. The blender's microprocessor (not shown) is pre-programed to start the mix motor 46 when the cup 22 is raised to a pre-determined height by the cupholder elevator assembly 30 and continue having the cupholder elevator assembly 30 raise the cup 22 to specified pre-determined heights during the blending process before eventually lowering the cup 22. These specified heights are determined based upon the cup 22 size. If a cup with an incorrect size is used, the mix motor 46 may start too soon or not soon enough. If the mix motor 46 does not start soon enough, the cupholder elevator assembly 30 or rotatable cutting blade 42 may be damaged as it tries to push a cup with frozen ingredients upward into a stationary sharp rotatable cutting blade 42. Similarly, if the cupholder elevator assembly 30 continues to move the cup 22 upward after the rotatable cutting blade 42 reaches the bottom of the cup 22, the rotatable cutting blade 42 will start cutting into the cup 22 itself and, in the process, mix cup shavings into the frozen product. To avoid such problems, the cup size light beam 146 acts in cooperation with an encoder 37 (see, FIG. 16) attached to the drive motor 32 to determine the cup 22 height. The drive motor encoder 37 counts how much the cup 22 is being raised from its base position as shown in FIG. 1. When the top of the cup 22 reaches the entrance 130 of the food preparation chamber 40, it blocks the cup size light beam 146. The cup size light beam sensor then sends a signal to the blender's microprocessor that the cup size light beam 146 has been interrupted. The microprocessor uses the accumulated encoder 37 count up to the point of interruption to calculate the cup 22 size. If the microprocessor determines the cup 22 size matches one of the pre-programmed cup sizes, the blending process is allowed to continue. If the microprocessor determines that the cup 22 size is incorrect, the microprocessor directs the cupholder elevator assembly 30 to lower the cup 22 back to its start position and alert the user of an error. In addition to using a cup 22 of the wrong size, an error signal will be triggered if the cup 22 is not correctly seated in the cupholder 20.

The blender 10 of the present invention can be used with multiple specific sizes of cups by pre-programming the microprocessor with acceptable cup heights. The microprocessor would then determine the blending process parameters (e.g., range of cup movement during blending cycle) based upon the detected cup 22 size.

The three remaining safety light beams 140, 142, 144 shown in FIG. 25 are used to detect any intrusion of foreign objects below the food preparation chamber 40 and, thereby, assure that a foreign object, such as a customer's hand, will not be pinched or otherwise damaged by the cupholder 20 and/or cantilevered cupholder connector 24 while they are traveling upward. If such a foreign object is detected at any time, a safety relay (not shown) will immediately stop both the mix motor 46 and drive motor 32. Additionally, if such a foreign object is detected when the cupholder elevator assembly 30 is not at its starting position, the microprocessor will display an error message on the optional video screen 14 and/or the control panel 16. Later, when all of the safety light beams 140, 142, 144 are no longer interrupted and the microprocessor determines that it is safe to proceed, the microprocessor will direct the cupholder elevator assembly 30 to return the cup 22 to the starting position. To avoid inadvertent interruption of the blending process, the safety light beams 140, 142, 144 are preferably configured so they will not be triggered when the cup 22 and cupholder 20 enter the food preparation chamber 40 along their expected path.

In the foregoing specification, the invention has been described with reference to specific preferred embodiments and methods. It will, however, be evident to those of skill in the art that various modifications and changes may be made without departing from the broader spirit and scope of the invention as set forth in the appended claims. The specification and drawings are, accordingly, to be regarded in an illustrative, rather than restrictive sense; the invention being limited only by the appended claims.

What is claimed is:

1. A method of operating a blender having a rotatable cutting blade in a food preparation chamber and a cupholder configured to receive a cup containing food to be blended, comprising:
   providing a sensing light assembly;
   generating a first sensing light beam and a second sensing light beam with the sensing light assembly;
   determining if a foreign object is located below the rotatable cutting blade using the first sensing light beam;
   generating a first error signal if the foreign object crosses the first sensing light beam;
   preventing or stopping rotation of the cutting blade in response to the first error signal;
   determining whether the cup is correctly seated in the cupholder using the second sensing light beam; and
   generating a second error signal if the cup is not correctly seated in the cupholder.

2. The method of claim 1, wherein the first sensing light beam is an infrared light beam.

3. The method of claim 1, wherein the sensing light assembly includes an emitter and a sensor.

4. The method of claim 3, wherein the first error signal is generated when the first sensing light beam is blocked as it travels between said emitter and said sensor.

5. The method of claim 1, wherein said first error signal causes any ongoing blending processes to immediately stop.

6. The method of claim 1, further comprising inserting the cup into the food preparation chamber by moving the cup from a base position to a raised position with a cupholder elevator assembly.

7. The method of claim 1, further comprising determining a size of the cup using the second sensing light beam.

8. The method of claim 1, wherein the second sensing light beam is an infrared light beam.

9. The method of claim 1, wherein the second error signal is generated if the cup is not detected by the second sensing light beam.

10. The method of claim 9, wherein the second sensing light beam is positioned so as not to interfere with the first sensing light beam.

11. The method of claim 7, wherein determining the size of the cup is based on feedback from both the second sensing light beam and an encoder.

12. The method of claim 1, further comprising providing, on a touch screen control panel, an error message to a user based on the first error signal.

13. A method of operating a blender having a rotatable cutting blade in a food preparation chamber and a touch screen control panel, comprising:
   providing a sensing light assembly;
   generating a first sensing light beam with the sensing light assembly, the first sensing light beam located outside of the food preparation chamber;
   generating a second sensing light beam with the sensing light assembly;
   inserting a cup containing food to be blended into the food preparation chamber;
   requesting an input from a user via the touch screen control panel, the input indicative of a desired consistency of a blended product;
   detecting a characteristic of the cup using the second sensing light beam;
   detecting if a foreign object is located below the rotatable cutting blade using the first sensing light beam;
   generating an error signal if the foreign object crosses the first sensing light beam; and
   preventing or stopping rotation of the cutting blade in response to the error signal.

14. The method of claim 13, further comprising providing an error message on the touch screen control panel based on the error signal.

15. The method of claim 13, wherein the first sensing light beam is an infrared light beam.

16. The method of claim 13, wherein the sensing light assembly includes an emitter and a sensor.

17. The method of claim 13, wherein said error signal causes any ongoing blending process to immediately stop, and wherein said error signal causes an error message to appear on the touch screen control panel.

18. The method of claim 13, wherein the second sensing light beam is configured to detect whether the cup is seated in a cupholder.

19. The method of claim 18, further comprising determining a size of the cup using the second sensing light beam and an encoder.

20. The method of claim 1, further comprising maintaining a separation between the cutting blade and the cup when the first error signal is generated.

21. The method of claim 13, further comprising maintaining a separation between the cutting blade and the cup when the error signal is generated.

* * * * *